(12) United States Patent
Yamaguchi et al.

(10) Patent No.: US 8,603,822 B2
(45) Date of Patent: Dec. 10, 2013

(54) METHOD FOR DESIGNING HEAT-RESISTANT TYROSINE-DEPENDENT SHORT-CHAIN DEHYDROGENASE/REDUCTASE AND HEAT-RESISTANT TYROSINE-DEPENDENT SHORT-CHAIN DEHYDROGENASE/REDUCTASE

(75) Inventors: Daisuke Yamaguchi, Kanagawa (JP); Seiji Yamada, Kanagawa (JP); Yoshio Goto, Kanagawa (JP); Yuichi Tokita, Kanagawa (JP)

(73) Assignee: Sony Corporation, Tokyo (JP)

( * ) Notice: Subject to any disclaimer, the term of this patent is extended or adjusted under 35 U.S.C. 154(b) by 255 days.

(21) Appl. No.: 13/013,239

(22) Filed: Jan. 25, 2011

(65) Prior Publication Data
US 2011/0212503 A1 Sep. 1, 2011

(30) Foreign Application Priority Data

Jan. 28, 2010 (JP) .................. 2010-016675

(51) Int. Cl.
| | |
|---|---|
| C12N 15/00 | (2006.01) |
| C12N 9/04 | (2006.01) |
| C12N 1/20 | (2006.01) |
| C12P 21/06 | (2006.01) |
| C12P 21/04 | (2006.01) |
| C12Q 1/68 | (2006.01) |
| C07H 21/04 | (2006.01) |

(52) U.S. Cl.
USPC ......... 435/440; 435/190; 435/69.1; 435/71.1; 435/6.1; 435/252.3; 435/320.1; 536/23.2

(58) Field of Classification Search
None
See application file for complete search history.

(56) References Cited

FOREIGN PATENT DOCUMENTS

| JP | 2004-071559 | 3/2004 |
| JP | 2007-143493 | 6/2007 |
| JP | 2008-048703 | 3/2008 |

OTHER PUBLICATIONS

Branden et al. Introduction to Protein Structure, Garland Publishing Inc., New York, p. 247, 1991.*
Yamaguchi et al. Development of thermostable gluconate 5-dehydrogenase for biofuel cell system. Abstract. 217$^{th}$ ECS Meeting, Abstract #401, Apr. 2010.*

\* cited by examiner

*Primary Examiner* — Yong Pak
(74) *Attorney, Agent, or Firm* — K&L Gates LLP

(57) ABSTRACT

A method for designing a heat-resistant mutant enzyme, the method including the step of reducing a distance between the α4 helix and the α6 helix in a protein three-dimensional structure to become smaller than that of a wild type enzyme through deletion, replacement, addition, or insertion of one or several amino acids in the amino acid sequence of the wild type enzyme with respect to tyrosine-dependent short-chain dehydrogenase/reductase.

3 Claims, 5 Drawing Sheets

RMSD: 0.194

RMSD: 0.202

RMSD: 0.233

RMSD: 0.611

METHOD FOR DESIGNING HEAT-RESISTANT TYROSINE-DEPENDENT SHORT-CHAIN DEHYDROGENASE/REDUCTASE AND HEAT-RESISTANT TYROSINE-DEPENDENT SHORT-CHAIN DEHYDROGENASE/REDUCTASE

CROSS REFERENCES TO RELATED APPLICATIONS

The present application claims priority to Japanese Priority Patent Application JP 2010-016675 filed in the Japan Patent Office on Jan. 28, 2010, the entire contents of which are hereby incorporated by reference.

BACKGROUND

The present application relates to a method for designing a heat-resistant tyrosine-dependent short-chain dehydrogenase/reductase and a heat-resistant tyrosine-dependent short-chain dehydrogenase/reductase. In particular, the present application relates to, for example, a method for obtaining a heat-resistant mutant tyrosine-dependent short-chain dehydrogenase/reductase by changing a protein structure.

Enzymes are in vivo catalysts which facilitate many reactions related to life support under a moderate condition in a living body smoothly. The enzymes undergo metabolic turnover in the living body, and are produced in the living body as necessary, so as to perform catalytic functions.

At present, technologies to use the enzymes outside the living body have become commercially practical or have been studied toward commercialization. The technologies to use the enzymes have been developed in various technical fields, for example, production of useful materials, production of energy-related materials, measurement or analysis, environmental conservation, and medical care. In relatively recent years, technologies related to an enzyme cell which is one type of fuel cells (refer to Japanese Unexamined Patent Application Publication No. 2004-71559, for example), an enzyme electrode, an enzyme sensor (a sensor to measure chemical materials through the use of enzyme reactions), and the like have also been proposed.

Regarding the technology of fuel cell, developments proceed from fuel cells in the related art, in which combustible materials, e.g., methanol and hydrogen, are used as fuels, to fuel cells in which compounds, e.g., glucose, with a higher level of safety are used as fuels. However, metal catalysts, e.g., platinum, effectively act on highly reactive compounds, e.g., methanol and hydrogen, having relatively simple structures, whereas the catalyst efficiencies of metal catalysts are very low with respect to compounds, e.g., glucose, exhibiting a low level of danger or toxicity and having low reactivity. Consequently, as described above, enzyme cells, in which enzymes are used as catalysts, have been proposed. The enzymes have high catalytic performance, exhibit excellent substrate specificity and stereoselectivity and, therefore, efficiently catalyze reactions of compounds, e.g., glucose, having low reactivity, so that a safe fuel cell can be realized by incorporating the enzyme in a electrode of a fuel cell.

In the case where the enzyme is used outside the living body, it is important that the activity of the enzyme is high and the enzyme reaction rate is high. Furthermore, it is also necessary that the stability against changes in environment is high and the durability of the activity is high. However, the chemical body of the enzyme is a protein and, therefore, there are problems in that denaturation due to heat, pH, or the like occurs easily, and the stability outside the living body is low as compared with the other chemical catalysts, e.g., metal catalysts. In order to address the problems, Japanese Unexamined Patent Application Publication No. 2007-143493 and Japanese Unexamined Patent Application Publication No. 2008-48703 disclose a mutant enzyme (diaphorase), wherein the levels of the activity and the heat resistance are raised to at least predetermined levels by changing artificially a base sequence of a gene coding a protein, so as to produce a mutant protein.

SUMMARY

The "tyrosine-dependent short-chain dehydrogenase/reductase" is a NAD(P)(H)-dependent short-chain dehydrogenase/reductase, and regarding the catalytic activity thereof, a tyrosine residue plays an important role (refer to "Short-chain dehydrogenases/reductases (SDR)", Biochemistry, 1995 May 9; 34(18): 6003-13, "Structure-function relationships of SDR hydroxysteroid dehydrogenases", Adv Exp Med Biol, 1997; 414: 403-15, and "The refined three-dimensional structure of 3 alpha,20 beta-hydroxysteroid dehydrogenase and possible roles of the residues conserved in short-chain dehydrogenases", Structure, 1994 Jul. 15; 2(7): 629-40). This enzyme group extends over a plurality of EC classes of short-chain dehydrogenases/reductases, lyase, and isomerase. In these classes, there are various enzymes which act on steroid, prostaglandin, aliphatic alcohols, and xenobiotics. The sequence identity among various enzymes included in this enzyme group is a low 10 to 30, but the three-dimensional structure are very resemble (refer to "Three-dimensional structure of holo 3 alpha,20 beta-hydroxysteroid dehydrogenase: a member of a short-chain dehydrogenase family", Proc Natl Acad Sci USA, 1991 Nov. 15; 88(22): 10064-8, "Molecular mechanisms of estrogen recognition and 17-keto reduction by human 17beta-hydroxysteroid dehydrogenase 1", Chem Biol Interact, 2001 Jan. 30; 130-132(1-3): 637-50, "A structural account of substrate and inhibitor specificity differences between two naphthol reductases", Biochemistry, 2001 Jul. 31; 40(30): 8696-704, "Structure-function relationships of SDR hydroxysteroid dehydrogenases", Adv Exp Med Biol, 1997; 414: 403-15, "Crystal structure of the ternary complex of mouse lung carbonyl reductase at 1.8 A resolution: the structural origin of coenzyme specificity in the short-chain dehydrogenase/reductase family", Structure, 1996 Jan. 15; 4(1): 33-45, "Crystal structures of the binary and ternary complexes of 7 alpha-hydroxysteroid dehydrogenase from *Escherichia coli*", Biochemistry, 1996 Jun. 18; 35(24): 7715-30, "Crystal structure of rat liver dihydropteridine reductase", Proc Natl Acad Sci USA, 1992 Jul. 1; 89(13): 6080-4, "Structural role of conserved Asn179 in the short-chain dehydrogenase/reductase scaffold", Biochem Biophys Res Commun, 2001 Dec. 7; 289(3) 712-7, and "A mechanism of drug action revealed by structural studies of enoyl reductase", Science, 1996 Dec. 20; 274(5295): 2107-10).

"Gluconate 5-dehydrogenase (Gn5DH)" is an enzyme belonging to the above-described tyrosine-dependent short-chain dehydrogenase/reductase family. Gn5DH is an enzyme that catalyzes a reaction in which two electrons are taken from gluconic acid and is given to NAD to generate NADH. In an enzyme cell, Gn5DH catalyzes a reaction in which an electron is taken from gluconic acid generated through oxidation of glucose due to a glucose dehydrogenase and is given to NAD to generate NADH.

It is desirable to provide a method for designing a mutant enzyme with a level of the heat resistance higher than or equal to a predetermined level in view of the wide-ranging availability of a tyrosine-dependent short-chain dehydrogenase/reductase and a gluconic acid dehydrogenase outside a living body.

A method for designing a heat-resistant mutant enzyme according to an embodiment includes the step of reducing a distance between the α4 helix and the α6 helix in a protein three-dimensional structure to become smaller than that of a wild type enzyme through deletion, replacement, addition, or insertion of one or several amino acids in the amino acid sequence of the wild type enzyme with respect to tyrosine-dependent short-chain dehydrogenase/reductase.

In this method for designing a heat-resistant mutant enzyme, the above-described tyrosine-dependent short-chain dehydrogenase/reductase may be especially a gluconic acid dehydrogenase.

A heat-resistant mutant tyrosine-dependent short-chain dehydrogenase/reductase according to another embodiment has a distance between the α4 helix and the α6 helix in a protein three-dimensional structure smaller than that of a wild type tyrosine-dependent short-chain dehydrogenase/reductase.

A heat-resistant mutant gluconic acid dehydrogenase according to another embodiment has an amino acid sequence indicated by Seq ID No. 1, in which one or several amino acids are subjected to deletion, replacement, addition, or insertion, wherein a distance between the α4 helix and the α6 helix in a protein three-dimensional structure is smaller than that of a wild type gluconic acid dehydrogenase having the amino acid sequence indicated by Seq ID No. 1. This heat-resistant mutant gluconic acid dehydrogenase may have an amino acid sequence indicated by any one of Seq ID Nos. 2, 11, 23, and 70. Regarding these heat-resistant mutant gluconic acid dehydrogenases, the residual enzyme activity after a heat treatment at 47.5° C. for 10 minutes may be 20% or more of the enzyme activity before the heat treatment.

Furthermore, in an electrochemical apparatus by using an enzyme according to another embodiment, the above-described enzyme is a heat-resistant mutant tyrosine-dependent short-chain dehydrogenase/reductase having a distance between the α4 helix and the α6 helix in the protein structure smaller than that of a wild type tyrosine-dependent short-chain dehydrogenase/reductase.

According to embodiments, a method for designing a mutant tyrosine-dependent short-chain dehydrogenase/reductase with a level of the heat resistance higher than or equal to a predetermined level is provided.

Additional features and advantages are described herein, and will be apparent from the following Detailed Description and the figures.

DETAILED DESCRIPTION

Figure 1:
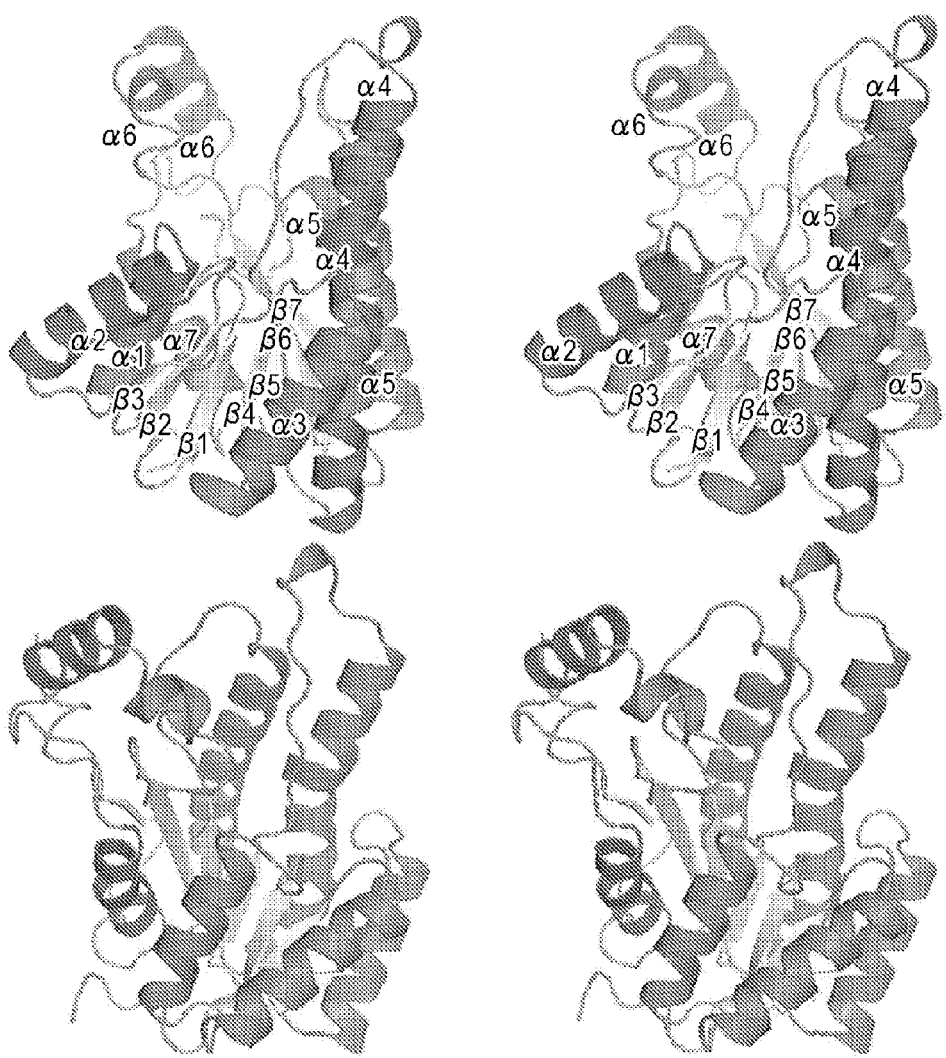
FIG. 1 is a two-dimensional structure stereo view of a wild type Gn5DH.
Figure 2A:
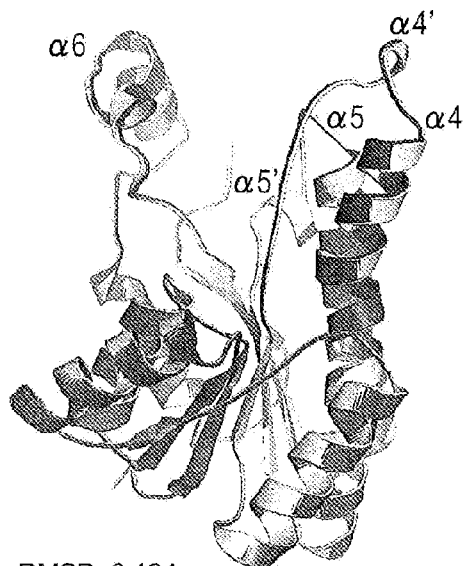
FIGS. 2A to 2D are diagrams showing superposed three-dimensional structures of a wild type Gn5DH and a mutant Gn5DH.
Figure 2B:
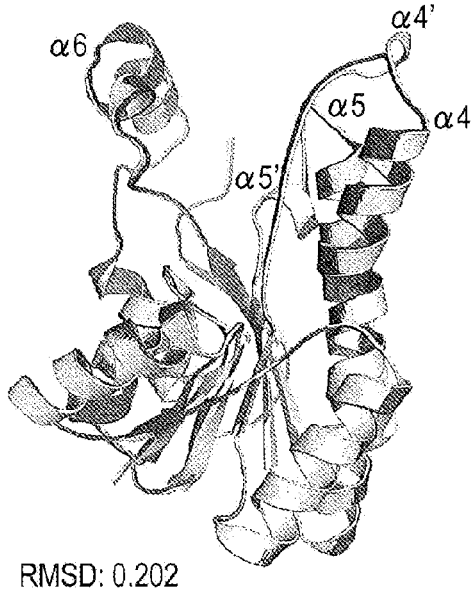
Figure 2C:
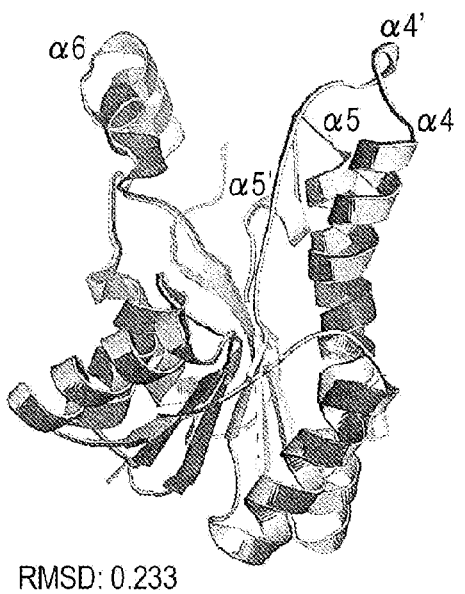
Figure 2D:
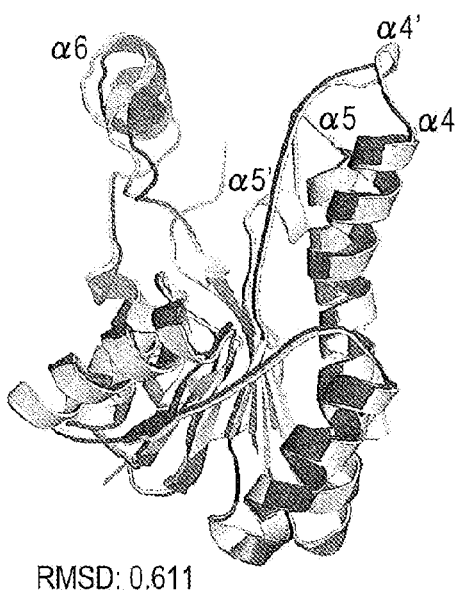

The present application will be described below in greater detail with reference to the drawings according to an embodiment.

The present inventors formed many heat-resistant mutants of gluconic acid dehydrogenase (Gn5DH) by using a genetic engineering technique and performed crystal structure analysis with X-rays. As a result, it was newly found that the heat resistance of the mutant Gn5DH was improved because a distance between the α4 helix and the α6 helix in a protein three-dimensional structure was reduced to become smaller than that of the wild type Gn5DH.

On the basis of this finding, a method for designing a heat-resistant mutant enzyme is provided according to embodiments, wherein the distance between the α4 helix and the α6 helix in the protein structure of Gn5DH is reduced to become smaller than that of the wild type enzyme.

This designing method is executed by using a general-purpose molecular design program and calculating the distance between the α4 helix and the α6 helix, where one or several amino acids in the amino acid sequence (refer to Seq ID No. 1) of the wild type Gn5DH are subjected to deletion, replacement, addition, or insertion.

Gn5DH has a structure similar to other enzymes belonging to the tyrosine-dependent short-chain dehydrogenase/reductase family and catalyzes an oxidation reduction reaction of a substrate dependently on a prosthetic group NAD(P)H (refer to "Crystal structures of the binary and ternary complexes of 7 alpha-hydroxysteroid dehydrogenase from *Escherichia coli*", Biochemistry, 1996 Jun. 18; 35(24): 7715-30, "Dramatic differences in the binding of UDP-galactose and UDP-glucose to UDP-galactose 4-epimerase from *Escherichia coli*", Biochemistry, 1998 Aug. 18; 37(33): 11469-77, "The catalytic reaction and inhibition mechanism of *Drosophila* alcohol dehydrogenase: observation of an enzyme-bound NAD-ketone adduct at 1.4 A resolution by X-ray crystallography", J Mol Biol, 1999 Jun. 4; 289(2): 335-55, and "Crystal residues for structure and catalysis in short-chain dehydrogenases/reductases", J Biol Chem, 2002 Jul. 12; 277(28): 25677-84, Epub 2002 Apr. 25). Therefore, the method for designing a heat-resistant mutant enzyme according to embodiments may be applied to not only Gn5DH, but also an enzyme group belonging to the tyrosine-dependent short-chain dehydrogenase/reductase family widely.

As for these enzyme groups, the following are mentioned. Protein Data Bank accession ID (three-dimensional structure coordinate data) are shown following the enzyme name.

Putative gluconate-5-dehydrogenase [1vl8], 3-Oxoacyl-(Acyl carrier protein) reductase [2uvd, 2pnf], β-Ketoacyl-(Acyl carrier protein) reductase [1q7b], Fatty acid synthase [1edo, 2cdh], α-Hydroxysteroid dehydrogenase [1ahi, 1ahh, 1fmc], D-3-Hydroxybutyrate dehydrogenase [2q2q, 2q2v, 2q2w], Glucose dehydrogenase [1gco, 1spx], Xylitol dehydrogenase [1zem], Sorbitol dehydrogenase [1k2w], (S)-specific 1-Phenylethanol dehydrogenase [2ew8], Xylulose reductase [1wnt], Tropinone reductase [1ae1], Mannitol dehydrogenase [1h5q], Haloalocohol dehydrogenase [1pwx, 1pwz, 1pxo, 1zmt, 1zo8].

A mutant enzyme obtained by the method for designing a heat-resistant mutant enzyme according to embodiments is provided with high heat resistance. Therefore, in technologies of production of useful materials, production of energy-related materials, measurement or analysis, environmental conservation, medical care, electrochemical apparatuses, and the like, a high enzyme reaction rate and high durability of the activity may be obtained by using this mutant enzyme. In particular, an enzyme cell which sustains production of a high output may be obtained by incorporating the mutant enzyme into a fuel electrode of the enzyme cell.

EXAMPLES

Example 1

1. Cloning, Manifestation, and Purification of Gluconic Acid Dehydrogenase (Gn5DH) Gene Derived from *Escherichia coli* K12

(1-1) Isolation and Purification of Genome DNA from *Escherichia coli* K12

*Escherichia coli* K12 is one strain of *Escherichia coli* that is widely used as a host in a recombinant DNA experiment. Regarding *Escherichia coli* K12, the most detailed chromosome map in the living world has been disclosed. After *Escherichia coli* K12 was cultured following the usual method, collection of bacteria through centrifugal separation was performed. Then, genome DNA was isolated by using Wizard Genomic DNA Purification Kit (Promega K.K.) (for details of the method, refer to an instruction manual attached to a product).

(1-2) Cloning of Gn5DH

The Gn5DH gene was amplified from the resulting genome DNA through PCR. The Gn5DH gene of *Escherichia coli* K12 is registered as Accession Number NC_000913 [REGION: complement(4490610.4491374)] in Nucleotide database of NCBI (http://www.ncbi.nlm.nih.gov/sites/entrez?db=nuccore&itool=toolbar) (refer to Seq ID No. 67).

As for DNA polymerase, Pfu DNA polymerase (Stratagene Corporation) was used, and a primer having a sequence shown in Table 1 described below was used. In this regard, the underlined portion shows a NdeI sequence (Forward primer) and a BamHI sequence (Reverse primer).

TABLE 1

| Forward primer | 5'-ggaattccat atgaacgatc tattttcact g-3' Seq ID No. 68 |
|---|---|
| Reverse primer | 5'-gcggatccett aaacagccac taacatgc-3' Seq ID No. 69 |

A PCR product of the Gn5DH gene was purified by using PCR Cleanup Kit (Qiagen), and identified by electrophoresis. The base sequence was identified with a DNA sequencer.

(1-3) Introduction of Gn5DH Gene into Vector

An amplified fragment of Gn5DH gene was treated with BamHI and NdeI and was purified by using PCR Cleanup Kit (Qiagen). A vector pET12a (Novagen) was treated with BamHI and NdeI and was purified in the same manner. These two types of fragments were ligated with T4 ligase, XL1-blue electrocompetent cell (Stratagene Corporation) was transformed with the resulting product, and culture was performed in an LB-amp culture medium to amplify.

The resulting plasmid was treated with BssHII, insertion of Gn5DH gene was identified by electrophoresis, and the base sequence was analyzed.

(1-4) Transformation of *Escherichia Coli*

A plasmid was introduced into *E. coli* BL21 (DE3) (Novagen) by a heat shock method to transform. Preculture was performed in SOC at 37° C. for 1 hour and, thereafter, development into an LB-amp agar culture medium was performed. A part of colony was liquid-cultured and manifestation of Gn5DH was identified by SDS-PAGE. Centrifugal separation of 3 mL of transformant culture fluid was performed. A 2xYT culture medium was added to *Escherichia coli* pellets, dispersion was effected, and preservation was performed at −80° C.

(1-5) Large-Scale Culture and Protein Purification

A frozen sample of a transformant was developed in an LB-amp agar culture medium, a colony was picked up, and preculture was performed with 100 mL of LB-amp until OD600 reached about 1. This was developed into 18 L of LB-amp, and shake culture was performed at 37° C. until OD600 was saturated at about 2. Bacterial cells were recovered from the resulting culture fluid through centrifugal separation (5 kG) (yield 20 g in a wet state). The bacterial cell pellets were frozen at −80° C. and, thereafter, were dissolved. An ultrasonic treatment was performed at 0° C. in 200 mL of 50 mM Tris-HCl, pH 8.0, 1 mM EDTA, 1 mM DTT, 1 mM PMSF solution to dissolve bacteria, and a solution fraction was recovered through centrifugal separation (9.5 kG).

The resulting solution was passed through a negative ion exchange column (Sepharose Q FastFlow, Amersham Bioscience), and a Gn5DH-containing fraction was recovered and concentrated by an ultrafiltration method (the amount of solution 20 mL, Centriplus centrifugal filter unit YM-30, Millipore). Subsequently, the resulting sample was passed through a gel filtration column (Sephacryl S-200, Amersham Bioscience) to collect a Gn5DH-containing fraction.

Example 2

2. Formation of Mutant Library of Gn5DH Gene Through Random Mutation and Screening of High-Activity, Heat-Resistant Mutant (First Generation)

(2-1) Error-Prone PCR with GeneMorph (Registered Trade Mark)

A gene library of Gn5DH mutant was formed through Error-prone PCR, this gene was introduced into a vector DNA to manifest in *Escherichia coli*. The "Error-prone PCR method" refers to a method for causing mutation in replicated DNA fragments at random by using an occurrence of base sequence misreading of DNA polymerase in a DNA fragment replication reaction through PCR. Various methods have been reported, and here, GeneMorph (registered trade mark) by Stratagene Corporation was selected among commercialized methods. As for Template DNA, the above-described plasmid incorporated with the Gn5DH gene of *Escherichia coli* K12 was used. Likewise, the primer used for cloning of this gene was used. PCR was performed following the manual of GeneMorph (registered trade mark).

(2-2) Introduction of Gn5DH Gene into Vector

The product of Error-prone PCR was subjected to a restriction enzyme treatment with NdeI and RamHI. After a reaction was effected at 37° C. for 2 hours, the reaction product was purified with Qiaquick PCR purification Kit (Qiagen). As for the vector, pET12a was subjected to the restriction enzyme treatment with NdeI and RamHI (at 37° C. for 2 hours) in a manner similar to that in the PCR product.

These products of the restriction enzyme treatment reaction were separated through low-melting point agarose gel electrophoresis, and the vector DNA in the corresponding open-circle state was purified by using Qiaquick Gel Extraction Kit (Qiagen). Subsequently, purified product of the restriction enzyme treatment of the vector was treated with alkaline phosphatase to dephosphorylate a 5' terminal. The reaction product was purified with Qiaquick PCR purification Kit (Qiagen). The thus obtained Error-prone PCR product (that is, Gn5DH mutant gene library) was ligated to the vector subjected to restriction enzyme and dephosphorylation treatment. As for the ligation reaction, Ligation Kit Mighty Mix (TAKARA BIO INC.) was used. The reaction product was purified by an ethanol precipitation method.

(2-3) Formation of Competent Cell and Transformation

As for a competent cell, an in-house prepared electrocompetent cell of BL21(DE3) was used. A frozen sample of 40 µL of the competent cell was melted on ice, and 0.5 µL of DNA sample having a concentration of about 1 µg/µL was mixed. The whole amount was set in an electroporation cuvette with a gap of 0.1 cm, and 1,800 kV of voltage was applied, so that transformation was effected. This was blended with 960 µL of SOC culture medium, and preculture was performed through shaking at 37° C. for 1 hour. The resulting culture fluid was inoculated on 5 to 50 µL LB-amp agar culture medium, and incubation was performed at 37° C. for a night.

(2-4) Screening

Single colonies on the agar culture medium were inoculated on their respective LB-amp liquid culture media (150 µL) of a 96-well plate by using toothpicks. Two wells were assigned to *Escherichia coli* for producing a wild type. The upper surface of the well plate was sealed with a gas permeable adhesive sheet (ABgene), an attached rid was further placed, and shake culture was performed at 37° C. for a night (about 14 hours). After 50 µL of each of the resulting culture fluids was mixed sufficiently with 15 µL of BugBuster (Novagen) in a fresh well plate through pipetting, a rid was placed on the plate, and incubation was performed at 25° C. for 30 minutes to dissolve the bacteria. Subsequently, 75 µL of 0.1 M Tris-HCl, pH 8.0 and 10 µL of 0.1 M NAD were added at room temperature. At this time, one of two wild type samples was separated as an unheated control sample into a microtube and was stored at room temperature. A plate was sealed with a commercially available OPP tape, and was heat-treated at 50° C. for 35 minutes (thermostat), followed by being stood to cool to room temperature. The separated sample was returned to the plate. Each sample was blended with 10 µL of 0.5 M sodium gluconate solution, 1 µL of 10 g/L diaphorase solution and, furthermore, 5 µL of 20 mM anthraquinone sulfonic acid (AQS) 20DMSO solution sequentially. The plate was sealed with an OPP tape, and agitation was performed with a vortex mixer for 5 seconds. The manner of color revelation was recorded with a camera, and samples exhibiting intense color development due to reduction of the above-described AQS as compared with the wild type sample were selected as heat resistant candidates. Regarding each of the specimens passed the screening, a part of the culture medium remaining on the 96 well plate was inoculated on 4.5 mL of LB culture medium. Culture was performed for a night, and a plasmid was purified, followed by preservation in a freezer. Moreover, inoculation was performed on 4 mL of culture medium separately, culture was performed until OD600 reached about 0.4. Bacteria were collected through centrifugal separation, and were suspended in 2 mL of 2xYT culture medium, followed by freezing and preservation at −80° C.

(2-5) Large-Scale Manifestation and Purification of Gn5DH Mutant

Each specimen on the 96 well plate was subjected to large-scale culture by a method explained in Example 1, and the Gn5DH mutant was purified.

(2-6) Enzyme Activity Evaluation Test

The enzyme activity of the purified Gn5DH was evaluated by detecting NADH generated through reaction between gluconate and NAD at 25° C. by using the absorbance at 340 nm ($\epsilon 340=6.3\times 10^3$ M-1cm-1). A reaction was started by putting 1 mL of 100 mM Tris-HCl, pH 8.0, 2 mM NAD, 10 mM gluconate aqueous solution into a UV cell (optical path length 10 cm, volume 1 mL) and adding Gn5DH thereto. The activity was determined on the basis of the gradient of a region in which the absorbance changed linearly immediately after starting. Here, the concentration of Gn5DH was determined on the basis of a calibration curve formed by a Bradford method through the use of fetal bovine serum albumin as a standard.

(2-7) Heat Resistance Test

After the enzyme solution was heat-treated, the above-described enzyme activity evaluation test was performed, and the enzyme activity remaining after the heat treatment ("residual enzyme activity") was measured. The heat treatment was performed by heating the enzyme solution with an aluminum block heater at 47.5° C. for 10 minutes, at 53° C. for 10 minutes, or at 57.5° C. for 10 minutes.

(2-8) Results

According to the results of the enzyme activity evaluation test and the heat resistance test (treatment at 47.5° C. for 10 minutes), Gn5DH mutants exhibited higher activity or higher heat resistance as compared with that of the wild type Gn5DH are shown in "Table 2". In Table 2, the "enzyme activity persistence" indicates a percentage of proportion of the activity remaining after the heat treatment relative to the activity before the heat treatment, where the activity evaluation tests were performed before and after the heat treatment under the same condition.

TABLE 2

| Seq ID No. | Type of mutant | Enzyme activity | Residual enzyme activity | Enzyme activity persistence |
|---|---|---|---|---|
| 1 | WT | 6.22 | 0.77 | 12.4 |
| 2 | I155T | 12.39 | 10.87 | 87.7 |
| 3 | A63V/V124I | 11.05 | 3.45 | 31.2 |
| 4 | V254L | 9.7 | 8.31 | 85.7 |
| 5 | T154S | 8.95 | 5.45 | 60.9 |
| 6 | C144G | 8.16 | 6.4 | 78.5 |
| 7 | T154N | 6.91 | 5.56 | 80.4 |
| 8 | F191I | 6.41 | 3.32 | 51.8 |
| 9 | V61L | 6.34 | 1.78 | 28 |
| 10 | I80F/M146I | 6.29 | 5.1 | 81.1 |
| 11 | M146I | 3.61 | 3.5 | 96.9 |
| 12 | G85C/A120G/V140I | 2.56 | 2.27 | 88.6 |
| 13 | D237E | 3.84 | 2.94 | 76.5 |
| 14 | F191I/D220E | 3.86 | 2.95 | 76.3 |
| 15 | E109D | 5.23 | 3.89 | 74.5 |
| 16 | A228G | 4.39 | 2.98 | 67.9 |
| 17 | G30S/H131R | 3.16 | 2.02 | 64.1 |
| 18 | N142I/F191L | 4.51 | 1.95 | 43.3 |
| 19 | K82T/P86T/G95A | 25.08 | 2.9 | 11.6 |
| 20 | G95A | 18.23 | 1.28 | 7 |
| 21 | E194K | 3.29 | 0.26 | 7.8 |

(A) High-Activity, Heat-Resistant Mutant Gn5DH

Regarding mutant Gn5DH having amino acid sequences of Seq ID Nos. 2 to 10, the enzyme activity and the enzyme activity persistence (heat resistance) were improved as compared with those of a wild type (WT) of Seq ID No. 1.

Regarding mutant Gn5DH indicated by Seq ID No. 2, isoleucine at the 155th position from terminal N in the wild type amino acid sequence of Seq ID No. 1 is replaced with threonine (indicated by a code "I155T"). Likewise, regarding mutant Gn5DH indicated by Seq ID No. 3, alanine at the 63rd position is replaced with valine and valine at the 124th position is replaced with isoleucine ("A63V/V124I"). Regarding mutant Gn5DH indicated by Seq ID No. 4, valine at the 254th position is replaced with leucine ("V254L"). Regarding mutant Gn5DH indicated by Seq ID No. 5, threonine at the 154th position is replaced with serine ("T154S"). Regarding mutant Gn5DH indicated by Seq ID No. 6, cysteine at the 144th position is replaced with glycine ("C144G"). Regarding mutant Gn5DH indicated by Seq ID No. 7, threonine at the 154th position is replaced with asparagine ("T154N"). Regarding mutant Gn5DH indicated by Seq ID No. 8, phenylalanine at the 191st position is replaced with isoleucine ("F191I"). Regarding mutant Gn5DH indicated by Seq ID No. 9, valine at the 61st position is replaced with leucine ("V61L"). Regarding mutant Gn5DH indicated by Seq ID No. 10, isoleucine at the 80th position is replaced with phenylalanine and methionine at the 146th position is replaced with isoleucine ("I80F/M146I").

(B) Heat-Resistant Mutant Gn5DH

Regarding mutant Gn5DH having amino acid sequences of Seq ID Nos. 11 to 18, the enzyme activity persistence (heat resistance) was improved as compared with that of the wild type (WT).

Regarding mutant Gn5DH indicated by Seq ID No. 11, methionine at the 146th position from terminal N in the wild type amino acid sequence of Seq ID No. 1 is replaced with isoleucine ("M146I"). Likewise, regarding mutant Gn5DH indicated by Seq ID No. 12, glycine at the 85th position is replaced with cysteine, alanine at the 120th position is replaced with glycine, and valine at the 140th position is replaced with isoleucine ("G85C/A120G/V140I"). Regarding mutant Gn5DH indicated by Seq ID No. 13, aspartic acid at the 237th position is replaced with glutamic acid ("D237E"). Regarding mutant Gn5DH indicated by Seq ID No. 14, phenylalanine at the 191st position is replaced with isoleucine and aspartic acid at the 220th position is replaced with glutamic acid ("F191I/D220E"). Regarding mutant Gn5DH indicated by Seq ID No. 15, glutamic acid at the 109th position is replaced with aspartic acid ("E109D"). Regarding mutant Gn5DH indicated by Seq ID No. 16, alanine at the 228th position is replaced with glycine ("A228G"). Regarding mutant Gn5DH indicated by Seq ID No. 17, glycine at the 30th position is replaced with serine and histidine at the 131st position is replaced with arginine ("G30S/H131R"). Regarding mutant Gn5DH indicated by Seq ID No. 18, asparagine at the 142nd position is replaced with isoleucine and phenylalanine at the 191st position is replaced with leucine ("N142I/F191L").

(C) High-Activity Mutant Gn5DH

Regarding mutant Gn5DH indicated by Seq ID No. 19 or 20, the enzyme activity was improved as compared with that of the wild type (WT).

Regarding mutant Gn5DH indicated by Seq ID No. 19, ricin at the 82nd position from terminal N in the wild type amino acid sequence of Seq ID No. 1 is replaced with threonine, proline at the 86th position is replaced with threonine, and glycine at the 95th position is replaced with alanine ("K82T/P86T/G95A"). Likewise, regarding mutant Gn5DH indicated by Seq ID No. 20, glycine at the 95th position is replaced with alanine ("G95A").

Example 3

3. Formation of Mutant Library of Gn5DH Gene Through Random Mutation and Screening of High-Activity, Heat-Resistant Mutant (Second Generation)

The mutant Gn5DH genes indicated by Seq ID Nos. 2 to 6, 11, 19, and 20, which exhibited especially excellent enzyme activity and enzyme activity persistence in Example 2, were used as Template DNA, the mutant gene library was formed again through Error-prone PCR, and the mutant library was prepared. Screening was performed by a heat treatment at a temperature of 58° C. for 45 minutes. The mutants passed the screening were assumed to be second generation mutants. As in Example 2, the second generation Gn5DH mutants were purified, and the enzyme activity evaluation test and the heat resistance test were performed.

According to the results of the enzyme activity evaluation test and the heat resistance test (treatment at 53° C. for 10 minutes), Gn5DH mutants exhibited higher activity or higher heat resistance as compared with that of the wild type Gn5DH are shown in "Table 3".

TABLE 3

| Seq ID No. | | Enzyme activity | Residual enzyme activity | Enzyme activity persistence |
|---|---|---|---|---|
| 1 | wt | 6.22 | 0.00 | 0.00 |
| 22 | G95A/M146I | 23.14 | 9.39 | 40.60 |
| 23 | H69R/K82T/P86T/G95A/M146I | 22.73 | 19.38 | 94.77 |
| 24 | A63V/K82T/P86T/G95A/T154S/D237E | 19.92 | 10.67 | 53.56 |
| 25 | K82T/P86T/G95A/M146I/V200A/V254L | 19.37 | 15.09 | 77.89 |
| 26 | K82T/P86T/G95A/M146I | 19.00 | 17.22 | 90.63 |
| 27 | E51K/G95A/M146I | 18.20 | 6.77 | 37.18 |
| 28 | T154S/V254L | 15.05 | 7.02 | 46.65 |
| 29 | T154S/D237E/V254L | 14.20 | 11.35 | 79.92 |
| 30 | D83E/G95A/V200A/V254L | 13.54 | 0.03 | 0.19 |
| 31 | C144G/A227T/V254L | 13.33 | 6.20 | 46.47 |
| 32 | C144G/V254L | 13.04 | 9.49 | 72.77 |
| 33 | F23L/C144G/E201D/V254L | 11.91 | 8.80 | 73.84 |
| 34 | F5Y/E51K/C144G/V254L | 11.86 | 4.14 | 34.90 |
| 35 | I80F/M146I/V254L | 11.52 | 5.82 | 50.48 |
| 36 | A63V/V124I/Q222H | 11.42 | 6.67 | 58.42 |
| 37 | K136M/C144G/E175K/V254L | 11.08 | 7.68 | 69.35 |
| 38 | H131R/C144G/S148G/V254L | 10.86 | 10.51 | 96.74 |
| 39 | A63V/R99C | 10.41 | 6.76 | 64.91 |
| 40 | L24I/I80F/M146I | 9.48 | 6.17 | 65.12 |
| 41 | H54R/A63V/E201V/V254L | 8.62 | 1.18 | 13.71 |
| 42 | H54L/H100Y/C144G/V254L | 8.39 | 4.88 | 58.13 |
| 43 | Q59E/K82T/P86T/G95A/T154S/V254L | 7.48 | 6.98 | 93.37 |
| 44 | E72V/I155T/V254L | 7.43 | 6.49 | 87.32 |
| 45 | A63V/I155T | 7.32 | 2.89 | 39.56 |
| 46 | K82T/P86T/G95A/I155T/V254L | 7.27 | 6.90 | 94.98 |
| 47 | F5Y/E51K/I155T/V254L | 6.97 | 6.13 | 88.03 |
| 48 | E51K/I155T/V254L | 6.95 | 6.51 | 93.64 |
| 49 | I155T/E194G | 6.79 | 2.77 | 40.89 |
| 50 | A63V/V124I/M146I | 6.64 | 5.05 | 76.10 |
| 51 | D3H/G57D/M146I/V254L | 5.79 | 5.10 | 88.16 |
| 52 | G95A/I155T/V254L | 5.35 | 4.12 | 77.02 |
| 53 | I155T/F230L | 5.35 | 4.12 | 77.02 |
| 54 | I155T/I225T/V254L | 4.29 | 3.49 | 81.38 |
| 55 | T103I/M146I | 4.21 | 3.25 | 77.26 |
| 56 | G28D/H69A/G95A/E194G/V254L | 4.12 | 2.45 | 59.40 |
| 57 | L24I/E47K/E51K/I155T/Y190F/E203K | 3.72 | 1.89 | 50.76 |
| 58 | I58F/C144G/E194G | 3.63 | 3.58 | 98.38 |
| 59 | F65Y/M146I/I155T/V254L | 3.42 | 3.19 | 93.15 |
| 60 | A63V/M146I | 3.40 | 2.08 | 61.05 |
| 61 | G9R/E56G/A63V/M146I/D237N | 3.34 | 2.95 | 88.28 |
| 62 | V61I/H69R/M146I | 3.31 | 1.30 | 39.26 |
| 63 | I80F/M146I/I155T | 2.68 | 2.58 | 96.28 |
| 64 | G95A/C144G/V254L | 2.37 | 2.03 | 85.86 |
| 65 | A63T/I155T | 1.02 | 0.14 | 13.71 |
| 66 | A63V/V124I/Q147H | 0.31 | 0.18 | 57.53 |

(D) High-Activity, Super Heat-Resistant Mutant Gn5DH

Regarding the wild type (WT) Gn5DH indicated by Seq ID No. 1, the residual enzyme activity after a heat treatment at 53° C. for 10 minutes was 0. On the other hand, mutant Gn5DH having amino acid sequences of Seq ID Nos. 22 to 50 exhibited the enzyme activity after the heat treatment as well and, in addition, exhibited high enzyme activity before the heat treatment as compared with that of the wild type Gn5DH.

These mutant Gn5DH have still higher heat resistance (super heat resistance) as compared with that of the first generation Gn5DH mutant serving as Template.

Regarding mutant Gn5DH indicated by Seq ID No. 22, glycine at the 95th position from terminal N in the wild type amino acid sequence of Seq ID No. 1 is replaced with alanine and methionine at the 146th position is replaced with isoleucine ("G95A/M146I"). Likewise, regarding mutant Gn5DH indicated by Seq ID No. 23, histidine at the 69th position is replaced with arginine, ricin at the 82nd position is replaced with threonine, proline at the 86th position is replaced with threonine, glycine at the 95th position is replaced with alanine, and methionine at the 146th position is replaced with isoleucine ("H69R/K82T/P86T/G95A/M146I"). Regarding mutant Gn5DH indicated by Seq ID No. 24, alanine at the 63rd position is replaced with valine, ricin at the 82nd position is replaced with threonine, proline at the 86th position is replaced with threonine, glycine at the 95th position is replaced with alanine, threonine at the 154th position is replaced with serine, and aspartic acid at the 237th position is replaced with glutamic acid ("A63V/K82T/P86T/G95A/T154S/D237E"). Regarding mutant Gn5DH indicated by Seq ID No. 25, ricin at the 82nd position is replaced with threonine, proline at the 86th position is replaced with threonine, glycine at the 95th position is replaced with alanine, methionine at the 146th position is replaced with isoleucine, valine at the 200th position is replaced with alanine, and valine at the 254th position is replaced with leucine ("K82T/P86T/G95A/M146I/V200A/V254L"). Regarding mutant Gn5DH indicated by Seq ID No. 26, ricin at the 82nd position is replaced with threonine, proline at the 86th position is replaced with threonine, glycine at the 95th position is replaced with alanine, and methionine at the 146th position is replaced with isoleucine ("K82T/P86T/G95A/M146I"). Regarding mutant Gn5DH indicated by Seq ID No. 27, glutamic acid at the 51st position is replaced with ricin, glycine at the 95th position is replaced with alanine, and methionine at the 146th position is replaced with isoleucine ("E51K/G95A/M146I"). Regarding mutant Gn5DH indicated by Seq ID No. 28, threonine at the 154th position is replaced with serine and valine at the 254th position is replaced with leucine ("T154S/V254L"). Regarding mutant Gn5DH indicated by Seq ID No. 29, threonine at the 154th position is replaced with serine, aspartic acid at the 237th position is replaced with glutamic acid, and valine at the 254th position is replaced with leucine ("T154S/D237E/V254L"). Regarding mutant Gn5DH indicated by Seq ID No. 30, aspartic acid at the 83rd position is replaced with glutamic acid, glycine at the 95th position is replaced with alanine, valine at the 200th position is replaced with alanine, and valine at the 254th position is replaced with leucine ("D83E/G95A/V200A/V254L"). Regarding mutant Gn5DH indicated by Seq ID No. 31, cysteine at the 144th position is replaced with glycine, alanine at the 227th position is replaced with threonine, and valine at the 254th position is replaced with leucine ("C144G/A227T/V254L"). Regarding mutant Gn5DH indicated by Seq ID No. 32, cysteine at the 144th position is replaced with glycine and valine at the 254th position is replaced with leucine ("C144G/V254L").

Regarding mutant Gn5DH indicated by Seq ID No. 33, phenylalanine at the 23rd position is replaced with leucine, cysteine at the 144th position is replaced with glycine, glutamic acid at the 201st position is replaced with aspartic acid, and valine at the 254th position is replaced with leucine ("F23L/C144G/E201D/V254L"). Regarding mutant Gn5DH indicated by Seq ID No. 34, phenylalanine at the 5th position is replaced with tyrosine, glutamic acid at the 51st position is replaced with ricin, cysteine at the 144th position is replaced with glycine, and valine at the 254th position is replaced with leucine ("F5Y/E51K/C144G/V254L"). Regarding mutant Gn5DH indicated by Seq ID No. 35, isoleucine at the 80th position is replaced with phenylalanine, methionine at the 146th position is replaced with isoleucine, and valine at the 254th position is replaced with leucine ("I80F/M146I/V254L"). Regarding mutant Gn5DH indicated by Seq ID No. 36, alanine at the 63rd position is replaced with valine, valine at the 124th position is replaced with isoleucine, and glutamine at the 222nd position is replaced with histidine ("A63V/V124I/Q222H"). Regarding mutant Gn5DH indicated by Seq ID No. 37, ricin at the 136th position is replaced with methionine, cysteine at the 144th position is replaced with glycine, glutamic acid at the 175th position is replaced with ricin, and valine at the 254th position is replaced with leucine ("K136M/C144G/E175K/V254L"). Regarding mutant Gn5DH indicated by Seq ID No. 38, histidine at the 131st position is replaced with arginine, cysteine at the 144th position is replaced with glycine, serine at the 148th position is replaced with glycine, and valine at the 254th position is replaced with leucine ("H131R/C144G/S148G/V254L"). Regarding mutant Gn5DH indicated by Seq ID No. 39, alanine at the 63rd position is replaced with valine and arginine at the 99th position is replaced with cysteine ("A63V/R99C"). Regarding mutant Gn5DH indicated by Seq ID No. 40, leucine at the 24th position is replaced with isoleucine, isoleucine at the 80th position is replaced with phenylalanine, and methionine at the 146th position is replaced with isoleucine ("L24I/I80F/M146I"). Regarding mutant Gn5DH indicated by Seq ID No. 41, histidine at the 54th position is replaced with arginine, alanine at the 63rd position is replaced with valine, glutamic acid at the 201st position is replaced with aspartic acid, and valine at the 254th position is replaced with leucine ("H54R/A63V/E201V/V254L"). Regarding mutant Gn5DH indicated by Seq ID No. 42, histidine at the 54th position is replaced with leucine, histidine at the 100th position is replaced with tyrosine, serine at the 144th position is replaced with glycine, and valine at the 254th position is replaced with leucine ("H54L/H100Y/C144G/V254L").

Regarding mutant Gn5DH indicated by Seq ID No. 43, glutamine at the 59th position is replaced with glutamic acid, ricin at the 82nd position is replaced with threonine, proline at the 86th position is replaced with threonine, glycine at the 95th position is replaced with alanine, threonine at the 154th position is replaced with serine, and valine at the 254th position is replaced with leucine ("Q59E/K82T/P86T/G95A/T154S/V254L"). Regarding mutant Gn5DH indicated by Seq ID No. 44, glutamic acid at the 72nd position is replaced with valine, isoleucine at the 155th position is replaced with threonine, and valine at the 254th position is replaced with leucine ("E72V/I155T/V254L"). Regarding mutant Gn5DH indicated by Seq ID No. 45, alanine at the 63rd position is replaced with valine and isoleucine at the 155th position is replaced with threonine ("A63V/I155T"). Regarding mutant Gn5DH indicated by Seq ID No. 46, ricin at the 82nd position is replaced with threonine, proline at the 86th position is replaced with threonine, glycine at the 95th position is replaced with alanine, isoleucine at the 155th position is replaced with threonine, and valine at the 254th position is replaced with leucine ("K82T/P86T/G95A/I155T/V254L"). Regarding mutant Gn5DH indicated by Seq ID No. 47, phenylalanine at the 5th position is replaced with tyrosine, glutamic acid at the 51st position is replaced with ricin, isoleucine at the 155th position is replaced with threonine, and valine at the 254th position is replaced with leucine ("F5Y/E51K/I155T/V254L"). Regarding mutant Gn5DH indicated by Seq ID No. 48, glutamic acid at the 51st position is replaced with ricin, isoleucine at the 155th position is replaced with threonine, and valine at the 254th position is replaced with leucine ("E51K/I155T/V254L"). Regarding mutant Gn5DH indicated by Seq ID No. 49, isoleucine at the 155th position is replaced with threonine and glutamic acid at the 194th position is replaced with glycine ("I155T/E194G"). Regarding mutant Gn5DH indicated by Seq ID No. 50, alanine at the 63rd position is replaced with valine, valine at the 124th position is replaced with isoleucine, and methionine at the 146th position is replaced with isoleucine ("A63V/V124I/M146I").

(E) Super Heat-Resistant Mutant Gn5DH

Furthermore, mutant Gn5DH having amino acid sequences of Seq ID Nos. 51 to 66 exhibited the enzyme activity after the heat treatment as well and the enzyme activity persistence (heat resistance) was improved as compared with that of the wild type (WT). These mutant Gn5DH have still higher heat resistance (super heat resistance) as compared with that of the first generation Gn5DH mutant serving as Template.

Regarding mutant Gn5DH indicated by Seq ID No. 51, aspartic acid at the 3rd position from terminal N in the wild type amino acid sequence of Seq ID No. 1 is replaced with histidine, glycine at the 57th position is replaced with aspartic acid, methionine at the 146th position is replaced with isoleucine, and valine at the 254th position is replaced with leucine ("D3H/G57D/M146I/V254L"). Likewise, regarding mutant Gn5DH indicated by Seq ID No. 52, glycine at the 95th position is replaced with alanine, isoleucine at the 155th position is replaced with threonine, and valine at the 254th position is replaced with leucine ("G95A/I155T/V254L"). Regarding mutant Gn5DH indicated by Seq ID No. 53, isoleucine at the 155th position is replaced with threonine and phenylalanine at the 230th position is replaced with leucine ("I155T/F230L"). Regarding mutant Gn5DH indicated by Seq ID No. 54, isoleucine at the 155th position is replaced with threonine, isoleucine at the 225th position is replaced with threonine, and valine at the 254th position is replaced with leucine ("I155T/I225T/V254L"). Regarding mutant Gn5DH indicated by Seq ID No. 55, threonine at the 103rd position is replaced with isoleucine and methionine at the 146th position is replaced with isoleucine ("T103I/M146I"). Regarding mutant Gn5DH indicated by Seq ID No. 56, glycine at the 28th position is replaced with aspartic acid, histidine at the 69th position is replaced with alanine, glycine at the 95th position is replaced with alanine, glutamic acid at the 194th position is replaced with glutamine, and valine at the 254th position is replaced with leucine ("G28D/H69A/G95A/E194G/V254L"). Regarding mutant Gn5DH indicated by Seq ID No. 57, leucine at the 24th position is replaced with isoleucine, glutamic acid at the 47th position is replaced with ricin, glutamic acid at the 51st position is replaced with ricin, isoleucine at the 155th position is replaced with threonine, tyrosine at the 190th position is replaced with phenylalanine, and glutamic acid at the 203rd position is replaced with ricin ("L24I/E47K/E51K/I155T/Y190F/E203K"). Regarding mutant Gn5DH indicated by Seq ID No. 58, isoleucine at the 58th position is replaced with phenylalanine, cysteine at the 144th position is replaced with glycine, and glutamic acid at the 194th position is replaced with glycine ("I58F/C144G/E194G").

Regarding mutant Gn5DH indicated by Seq ID No. 59, phenylalanine at the 65th position is replaced with tyrosine, methionine at the 146th position is replaced with isoleucine, isoleucine at the 155th position is replaced with threonine, and valine at the 254th position is replaced with leucine ("F65Y/M146I/I155T/V254L"). Regarding mutant Gn5DH indicated by Seq ID No. 60, alanine at the 63rd position is replaced with valine and methionine at the 146th position is replaced with isoleucine ("A63V/M146I"). Regarding mutant Gn5DH indicated by Seq ID No. 61, glycine at the 9th position is replaced with arginine, glutamic acid at the 56th position is replaced with glycine, alanine at the 63rd position is replaced with valine, methionine at the 146th position is replaced with isoleucine, and aspartic acid at the 237th position is replaced with asparagine ("G9R/E56G/A63V/M146I/D237N"). Regarding mutant Gn5DH indicated by Seq ID No. 62, valine at the 61st position is replaced with isoleucine, histidine at the 69th position is replaced with arginine, and methionine at the 146th position is replaced with isoleucine ("V61I/H69R/M146I"). Regarding mutant Gn5DH indicated by Seq ID No. 63, isoleucine at the 80th position is replaced with phenylalanine, methionine at the 146th position is replaced with isoleucine, and isoleucine at the 155th position is replaced with leucine ("I80F/M146I/I155L"). Regarding mutant Gn5DH indicated by Seq ID No. 64, glycine at the 95th position is replaced with alanine, cysteine at the 144th position is replaced with glycine, and valine at the 254th position is replaced with leucine ("G95A/C144G/V254L"). Regarding mutant Gn5DH indicated by Seq ID No. 65, alanine at the 63rd position is replaced with threonine and isoleucine at the 155th position is replaced with threonine ("A63T/I155T"). Regarding mutant Gn5DH indicated by Seq ID No. 66, alanine at the 63rd position is replaced with valine, valine at the 124th position is replaced with isoleucine, and glutamine at the 147th position is replaced with histidine ("A63V/V124I/Q147H").

Example 4

4. Formation of Mutant Library of Gn5DH Gene Through Random Mutation and Screening of High-Activity, Heat-Resistant Mutant (Third Generation)

The mutant Gn5DH genes exhibited especially excellent enzyme activity and enzyme activity persistence in Example 3 were used as Template DNA, the mutant gene library was formed again through Error-prone PCR, and the mutant library was prepared. Screening of third generation mutants was performed. As in Example 3, the third generation Gn5DH mutants were purified, and the enzyme activity evaluation test and the heat resistance test were performed.

According to the results of the enzyme activity evaluation test and the heat resistance test (treatment at 57.5° C. for 10 minutes), Gn5DH mutants exhibited higher activity or higher heat resistance as compared with that of the wild type Gn5DH are shown in "Table 4".

TABLE 4

| Seq ID No. | | Enzyme activity | Residual enzyme activity | Enzyme activity persistence |
|---|---|---|---|---|
| 1 | WT | 7.6 | 0.0 | 0 |
| 70 | H69R K82T P86T G95A E109D M146I | 30.9 | 27.1 | 88 |
| 71 | H69R K82T P86T G95A M146I V254L | 20.5 | 16.4 | 80 |

TABLE 4-continued

| Seq ID No. | | Enzyme activity | Residual enzyme activity | Enzyme activity persistence |
|---|---|---|---|---|
| 72 | A63V K82T P86T G95A H131R C144G S148C V254L | 12.5 | 12.2 | 98 |
| 73 | K82T P86T H131R C144G S148C E203V V254L | 11.9 | 11.4 | 96 |
| 74 | I12V T42L E44K K82T P86T G95A E134G I155T V254L | 11.1 | 10.0 | 89 |
| 75 | K82T P86T H131R C144G S148C V254L | 10.8 | 10.4 | 96 |
| 76 | K82T P86T G95A I155T G163R F191I V254L | 10.4 | 8.8 | 85 |
| 77 | A63V K82T P86T G95A H131R C144G S148C K234R G248L V254L | 9.0 | 8.3 | 93 |
| 78 | H69R K82T P86T G95A I155T M250L V254L | 8.7 | 8.7 | 100 |
| 79 | L25M I155T K234T V254L | 8.5 | 7.9 | 92 |
| 80 | Q35L H69R K82T P86T G95A A120G M146I F191L V254L | 8.3 | 8.5 | 102 |
| 81 | P86H H131R C144G S148C V254L | 8.2 | 7.6 | 93 |
| 82 | A63V K82T P86T G95A D112E I155T V254L | 8.2 | 7.6 | 92 |
| 83 | H69R K82T P86T H131R C144G S148C V254L | 8.1 | 7.7 | 96 |
| 84 | K82T P86T G95A E109D I155T V254L | 8.0 | 7.7 | 97 |
| 85 | I155T V254L | 8.0 | 7.0 | 88 |
| 86 | H69R K82T I84F P86T G95A I155T V254L | 7.8 | 7.8 | 100 |
| 87 | H69R K82T P86T H131R C144G S148C V200A V254L | 7.2 | 6.7 | 93 |
| 88 | A63V K82T P86T G95A I155T D237E V254L | 7.1 | 6.4 | 90 |
| 89 | A63V H131R C144G S148C V254L | 7.0 | 6.6 | 95 |
| 90 | E56D K82T P86T G95A I155T V254L | 6.9 | 5.7 | 83 |
| 91 | Q59E A63V K82T P86T G95A I155T E203D V254L | 6.6 | 5.8 | 87 |
| 92 | H69R K82T P86T G95A I155T V254L | 6.2 | 5.8 | 93 |
| 93 | H69R K82T P86T G95A R99L I155T V254L | 6.2 | 5.8 | 94 |
| 94 | L48P F122S H131R C144G S148C V254L | 6.1 | 5.7 | 94 |
| 95 | T42A E78D K82T P86T G95A I155T F230Y V254L | 6.0 | 2.0 | 34 |
| 96 | Q59E K82T P86T G95A M146I I155T G248L V254L | 5.8 | 5.7 | 97 |
| 97 | Q59E K82T P86T G95A A137T M146I I155T F230S V254L | 5.8 | 5.6 | 96 |
| 98 | K82T P86T G95A M146I I155T V254L | 5.5 | 5.3 | 97 |
| 99 | K82T P86T G95A I155T D237E V254L | 5.2 | 4.9 | 93 |
| 100 | E51D A63V D83N N93T H100F D112E H131R C144G S148C A228G V254L | 4.9 | 4.7 | 97 |
| 101 | H69R K82T P86T G95A V128I H131R C144G S148C K192I V254L | 4.5 | 4.3 | 95 |
| 102 | K82T P86T G95A I155T V200A V254L | 4.3 | 3.6 | 85 |
| 103 | Q59E C144G S148C I155T G248L V254L | 3.7 | 3.4 | 92 |
| 104 | G95S I155T V254L | 2.4 | 2.3 | 92 |
| 105 | H69R K82T P86T G95A M146I I155L | 0.8 | 0.8 | 98 |
| 106 | G95A M146I I155L V254L | 0.1 | 0.1 | 99 |

(F) High-Activity, Ultra Super Heat-Resistant Mutant Gn5DH

Regarding the wild type (WT) Gn5DH indicated by Seq ID No. 1, the residual enzyme activity after a heat treatment at 57.5° C. for 10 minutes was 0. On the other hand, mutant Gn5DH having amino acid sequences of Seq ID Nos. 70-76 exhibited the enzyme activity after the heat treatment as well and, in addition, exhibited high enzyme activity before the heat treatment as compared with that of the wild type Gn5DH. These mutant Gn5DH have still higher heat resistance (ultra super heat resistance) as compared with that of the second generation Gn5DH mutant serving as Template.

(G) Ultra Super Heat-Resistant Mutant Gn5DH

Furthermore, mutant Gn5DH having amino acid sequences of Seq ID Nos. 77 to 106 exhibited the enzyme activity after the heat treatment as well and the enzyme activity persistence (heat resistance) was improved as compared with that of the wild type (WT). These mutant Gn5DH have still higher heat resistance (ultra super heat resistance) as compared with that of the second generation Gn5DH mutant serving as Template.

Example 5

5. X-Ray Crystal Structure Analysis of Wild Type Gn5DH and Mutant Gn5DH (5-1) Determination of Crystal Structure The wild type Gn5DH and the mutant Gn5DH exhibited especially excellent enzyme activity and enzyme activity persistence in Examples 2 to 4 were subjected to crystal structure analysis with X-rays.

The wild type Gn5DH and the mutant Gn5DH were purified following the method explained in the item "(1-5) Large-scale culture and protein purification" in Example 1. As for the mutant Gn5DH, the "high-activity, heat-resistant mutants" indicated by Seq ID Nos. 2 and 4, "heat-resistant mutant" indicated by Seq ID No. 11, the "high-activity mutant" indicated by Seq ID No. 20, the "high-activity, super heat-resistant mutant" indicated by Seq ID No. 23, and the "high-activity, ultra super heat-resistant mutant" indicated by Seq ID No. 70 were used (refer to Table 5).

TABLE 5

| Seq ID No. | Enzyme activity ($s^{-1}$) | $T_m$/ °C.($\Delta T_m$/° C.)* | Mutation site |
|---|---|---|---|
| 1 | 6.22 | 40.6 | WT |
| 2 | 12.39 | 52.5(+6.5) | I155T |
| 11 | 3.61 | 54.0(+8.0) | M146I |
| 23 | 22.73 | 56.5(+10.5) | H69R, K82T, P86T, G95A, M146I |
| 70 | 30.9 | 61.0(+15) | H69R, K82T, P86T, G95A, E109D, M146I |

(In Table, the term "$T_m$" represents a mutation midpoint temperature (a temperature at which the enzyme activity measured after the 10-minute heat treatment reaches a half of the enzyme activity before the heat treatment). The term "$\Delta T_m$" represents an increment of mutation midpoint temperature as compared with that of the wild type (WT).)

Equal amounts of the wild type or mutant Gn5DH solution (25 mg/mL in 20 mM Tris-Hcl, pH 8.0, 1.0 mM NAD) and a commercially available crystallization screening kit (Cryo I & II, Crystal Screen 1 & 2, Wizard I & II, Cryo I & II, PEG-ION/Foot Print Screen or Crystal Screen Cryo/Wizard III (Emerald BioSystems)) were mixed. The mixed solution was stood at 20° C. by a sitting drop vapor diffusion method and a hanging drop vapor diffusion method. As a result, hexagonal crystals were obtained.

X-ray diffraction spot data of each crystal was acquired by using an imaging plate X-ray detector R-AXIS IV++ (RIGAKU Corporation) and Crystal Clear ver. 1.3.5. Subsequently, structure refinement was performed with software programs CCP4 and Coot for modeling a protein crystal structure. The structure of the wild type Gn5DH was determined by using the Gn5DH coordinate (PDB ID: 1VL8), serving as a search model, derived from *Thermotoga maritima* belonging to a tyrosine-dependent short-chain dehydrogenase/reductase family similarly to Gn5DH derived from the *Escherichia coli*. The structure of each mutant Gn5DH was determined in the same manner while the structure of the wild type Gn5DH served as a template.

FIG. 1 shows a two-dimensional structure stereo view of a wild type Gn5DH. In FIG. 1, α1 to α7 indicate positions of α helix structures in that order from the N terminal side. Furthermore, β1 to β7 indicate positions of 13 sheet structures in that order from the N terminal side.

(5-2) Comparison of Crystal Structure

The difference in disposition of main chain between the structures of a wild type Gn5DH and a mutant Gn5DH was evaluated on the basis of α carbon ($C_\alpha$) least square fitting. As for the evaluation, LSQ Superimpose of Coot was used.

FIGS. 2A to 2D show three-dimensional structures of a wild type Gn5DH and a mutant Gn5DH in the state in which each mutant Gn5DH is superposed on a wild type Gn5DH. FIG. 2A to FIG. 2D are diagrams in which the mutant Gn5DH indicated by Seq ID Nos. 2, 11, 23, and 70, respectively, are superposed on the wild type Gn5DH. In the drawings, white indicates the wild type Gn5DH and black indicates the mutant Gn5DH. In this regard, the term "RMSD" indicates the value of $C_\alpha$ root mean square deviation (R.m.s.d $C_\alpha$).

FIGS. 3A to 3D show R.m.s.d $C_\alpha$ of each mutant Gn5DH related to the wild type Gn5DH on an amino acid residue unit basis. FIGS. 3A to 3D show the values of R.m.s.d $C_\alpha$ of mutant Gn5DH indicated by Seq ID Nos. 2, 11, 23, and 70, respectively. In the drawings, the horizontal axis indicates the amino acid residue number and the vertical axis indicates R.m.s.d $C_\alpha$.

As is clear from FIGS. 2A to 2D, the increasing order of R.m.s.d $C_\alpha$ of mutant Gn5DH is Seq ID Nos. 2, 11, 23, and 70, and the heat resistance is improved as the degree of change in structure from the wild type Gn5DH increases (refer to Table 5).

Figure 3A:
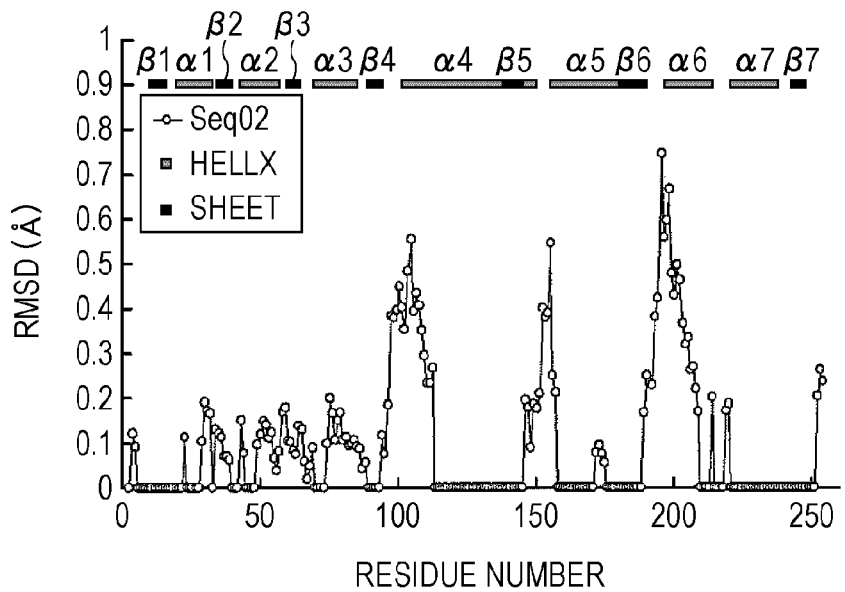
FIGS. 3A to 3D are diagrams showing R.m.s.d Cα of each mutant Gn5DH related to the wild type Gn5DH on an amino acid residue unit basis.
Figure 3B:
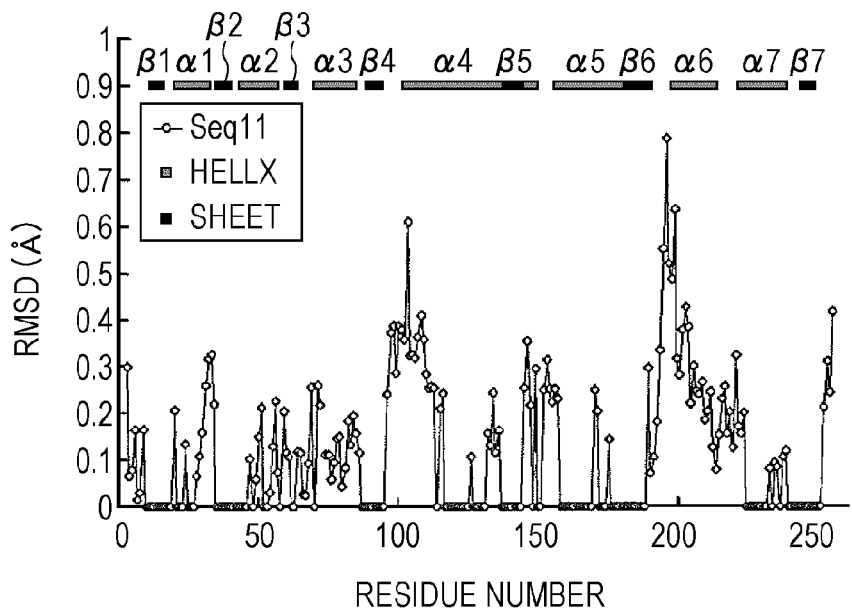
Figure 3C:
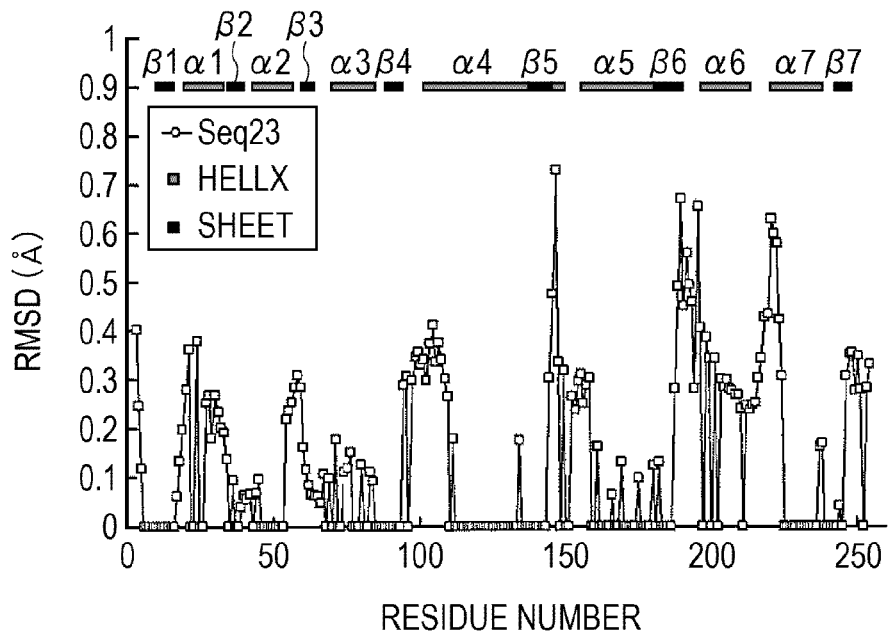
Figure 3D:
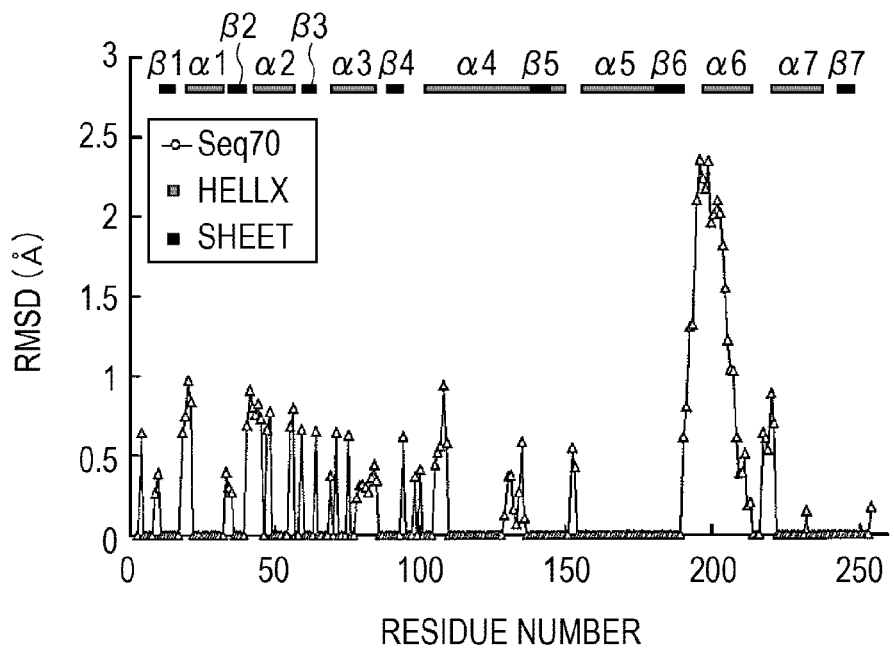

As shown in FIG. 3A, regarding the mutant Gn5DH indicated by Seq ID No. 2, changes in structure of α4, α5, and α6 helixes from the wild type Gn5DH were large. Furthermore, changes in structure of α4 and α6 helixes of the mutant Gn5DH indicated by Seq ID No. 11, α5 and α6 helixes of the mutant Gn5DH indicated by Seq ID No. 23, and an α6 helix of the mutant Gn5DH indicated by Seq ID No. 70 from the wild type Gn5DH were large (refer to FIGS. 3B to 3D). Consequently, it was assumed that regarding the mutant Gn5DH, the structures of the α4 to α6 helixes contributed to the heat resistance.

Example 6

6. Analysis of Change in Structure of Mutant Gn5DH

A change in structure of the mutant Gn5DH from that of the wild type Gn5DH was further analyzed on the basis of the distance between the α4 helix and the α6 helix serving as an indicator.

Figure 4:
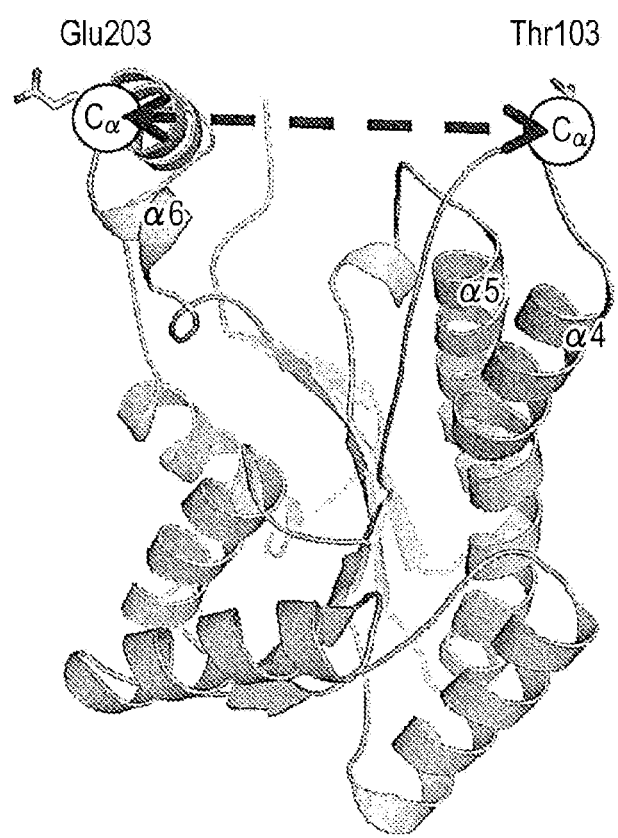
FIG. 4 is a diagram for explaining the definition of a distance between an α4 helix and an α6 helix.

The index of the distance between the α4 helix and the α6 helix was assumed to be the distance between the $C_\alpha$ of threonine 103 (Thr103) and the $C_\alpha$ of glutamic acid 203 (Glu203) which was the largest distance (refer to an arrow indicated by a broken line in FIG. 4).

"Table 6" shows the distances between the α4 helix and the α6 helix in the wild type Gn5DH and the mutant Gn5DH indicated by Seq ID Nos. 2, 11, 23, and 70.

TABLE 6

|  | Distance (Å) | Δdistance (Å) |
|---|---|---|
| WT | 29.82 | — |
| Seq ID No. 2 | 29.05 | −0.77 |
| Seq ID No. 11 | 29.04 | −0.78 |
| Seq ID No. 23 | 29.42 | −0.4 |
| Seq ID No. 70 | 28.13 | −1.69 |

As shown in Table, the distance of the α4 helix and the α6 helix in each mutant Gn5DH was smaller than that in the wild type Gn5DH. As is clear from this result, regarding the mutant Gn5DH, the heat resistance was improved because of reduction in the distance between the α4 helix and the α6 helix.

It is believed that a molecular structure becomes compact because of reduction in distance between the α4 helix and the α6 helix and, thereby, the heat resistance is improved. More specifically, it is believed that the volume of amino acid residue in the inside of the three-dimensional structure decreases, hydrogen bonds are formed between α4, α5, and α6 helixes through amino acid replacement and, thereby, a molecular structure becomes compact and the heat resistance is improved.

SEQUENCE LISTING

201001281358367500_A163_0990306604_
12010016675_AAA_6.app

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A method for designing a heat-resistant mutant enzyme, the method comprising:

reducing a distance between α4 helix and α6 helix in a protein three-dimensional structure to become smaller than that of a wild type gluconic acid dehydrogenase-through deletion, replacement, addition, or insertion of one or several amino acids in the amino acid sequence of the wild type enzyme with respect to tyrosine-dependent short-chain dehydrogenase/reductase;

and wherein the heat resistant mutant enzyme has an amino acid sequence selected from the group consisting of Seq ID Nos. 2-66 and 70-106.

2. The method according to claim 1, wherein the heat resistant mutant enzyme has an amino acid sequence selected from the group consisting of Seq ID Nos. 2, 11, 23, and 70.

3. The method according to claim 1, wherein the heat resistant mutant enzyme has a residual enzyme activity after a heat treatment at 47.5° C. for 10 minutes is at least 20% of the enzyme activity before the heat treatment.

* * * * *

SEQUENCE LISTING

<160> NUMBER OF SEQ ID NOS: 106

<210> SEQ ID NO 1
<211> LENGTH: 254
<212> TYPE: PRT
<213> ORGANISM: Escherichia coli

<400> SEQUENCE: 1

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250
```

<210> SEQ ID NO 2
<211> LENGTH: 254
<212> TYPE: PRT
<213> ORGANISM: Artificial
<220> FEATURE:
<223> OTHER INFORMATION: Synthesized: I155T mutation

<400> SEQUENCE: 2

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
```

```
                    100                 105                 110
Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
                195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 3
<211> LENGTH: 254
<212> TYPE: PRT
<213> ORGANISM: Artificial
<220> FEATURE:
<223> OTHER INFORMATION: Synthesized: A63V/V124I mutations

<400> SEQUENCE: 3

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Val Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Gln Glu Trp Asn Asp
            100                 105                 110

Val Ile Ala Val Asn Gln Thr Ala Val Phe Leu Ile Ser Gln Ala Val
            115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
                195                 200                 205

Leu Cys Lys Arg Thr Pro Ala Ala Arg Trp Gly Asp Pro Gln Glu Leu
            210                 215                 220
```

```
Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 4
<211> LENGTH: 254
<212> TYPE: PRT
<213> ORGANISM: Artificial
<220> FEATURE:
<223> OTHER INFORMATION: Synthesized: V254L mutation

<400> SEQUENCE: 4

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 5
<211> LENGTH: 254
<212> TYPE: PRT
<213> ORGANISM: Artificial
<220> FEATURE:
<223> OTHER INFORMATION: Synthesized: T154S mutation

<400> SEQUENCE: 5

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30
```

```
Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Pro
 50                  55                  60

Phe Asn Val Thr His Lys His Glu Ile Asp Ala Val Glu His Ile
 65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
                115                 120                 125

Thr Arg His Met Val Glu Arg Lys Ala Gly Lys Val Ile Asn Ile Cys
            130                 135                 140

Ser Met Gln Ser Glu Leu Gly Arg Asp Ser Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 6
<211> LENGTH: 254
<212> TYPE: PRT
<213> ORGANISM: Artificial
<220> FEATURE:
<223> OTHER INFORMATION: Synthesized: C144G mutation

<400> SEQUENCE: 6

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Pro
 50                  55                  60

Phe Asn Val Thr His Lys His Glu Ile Asp Ala Val Glu His Ile
 65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
                115                 120                 125

Thr Arg His Met Val Glu Arg Lys Ala Gly Lys Val Ile Asn Ile Gly
            130                 135                 140
```

```
Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250
```

<210> SEQ ID NO 7
<211> LENGTH: 254
<212> TYPE: PRT
<213> ORGANISM: Artificial
<220> FEATURE:
<223> OTHER INFORMATION: Synthesized: T154N mutation

<400> SEQUENCE: 7

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Met Gln Ser Glu Leu Gly Arg Asp Asn Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250
```

```
<210> SEQ ID NO 8
<211> LENGTH: 254
<212> TYPE: PRT
<213> ORGANISM: Artificial
<220> FEATURE:
<223> OTHER INFORMATION: Synthesized: F191I mutation

<400> SEQUENCE: 8

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Ile Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 9
<211> LENGTH: 254
<212> TYPE: PRT
<213> ORGANISM: Artificial
<220> FEATURE:
<223> OTHER INFORMATION: Synthesized: V61L mutation

<400> SEQUENCE: 9

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Leu Ala Ala Pro
        50                  55                  60

Phe Asn Val Thr His Lys His Glu Ile Asp Ala Ala Val Glu His Ile
```

-continued

```
                65                  70                  75                  80
Glu Lys Asp Ile Gly Pro Ile Asp Val Leu Val Asn Asn Ala Gly Ile
                    85                  90                  95
Gln Arg Arg His Pro Phe Thr Glu Phe Pro Glu Gln Glu Trp Asn Asp
                100                 105                 110
Val Ile Ala Val Asn Gln Thr Ala Val Phe Leu Val Ser Gln Ala Val
                115                 120                 125
Thr Arg His Met Val Glu Arg Lys Ala Gly Lys Val Ile Asn Ile Cys
            130                 135                 140
Ser Met Gln Ser Glu Leu Gly Arg Asp Thr Ile Thr Pro Tyr Ala Ala
145                 150                 155                 160
Ser Lys Gly Ala Val Lys Met Leu Thr Arg Gly Met Cys Val Glu Leu
                165                 170                 175
Ala Arg His Asn Ile Gln Val Asn Gly Ile Ala Pro Gly Tyr Phe Lys
                180                 185                 190
Thr Glu Met Thr Lys Ala Leu Val Glu Asp Glu Ala Phe Thr Ala Trp
                195                 200                 205
Leu Cys Lys Arg Thr Pro Ala Ala Arg Trp Gly Asp Pro Gln Glu Leu
            210                 215                 220
Ile Gly Ala Ala Val Phe Leu Ser Ser Lys Ala Ser Asp Phe Val Asn
225                 230                 235                 240
Gly His Leu Leu Phe Val Asp Gly Gly Met Leu Val Ala Val
                245                 250

<210> SEQ ID NO 10
<211> LENGTH: 254
<212> TYPE: PRT
<213> ORGANISM: Artificial
<220> FEATURE:
<223> OTHER INFORMATION: Synthesized: I80F/M146I mutations

<400> SEQUENCE: 10

Met Asn Asp Leu Phe Ser Leu Ala Gly Lys Asn Ile Leu Ile Thr Gly
1               5                   10                  15
Ser Ala Gln Gly Ile Gly Phe Leu Leu Ala Thr Gly Leu Gly Lys Tyr
                20                  25                  30
Gly Ala Gln Ile Ile Ile Asn Asp Ile Thr Ala Glu Arg Ala Glu Leu
            35                  40                  45
Ala Val Glu Lys Leu His Gln Glu Gly Ile Gln Ala Val Ala Ala Pro
        50                  55                  60
Phe Asn Val Thr His Lys His Glu Ile Asp Ala Val Glu His Phe
65                  70                  75                  80
Glu Lys Asp Ile Gly Pro Ile Asp Val Leu Val Asn Asn Ala Gly Ile
                85                  90                  95
Gln Arg Arg His Pro Phe Thr Glu Phe Pro Glu Gln Glu Trp Asn Asp
                100                 105                 110
Val Ile Ala Val Asn Gln Thr Ala Val Phe Leu Val Ser Gln Ala Val
                115                 120                 125
Thr Arg His Met Val Glu Arg Lys Ala Gly Lys Val Ile Asn Ile Cys
            130                 135                 140
Ser Ile Gln Ser Glu Leu Gly Arg Asp Thr Ile Thr Pro Tyr Ala Ala
145                 150                 155                 160
Ser Lys Gly Ala Val Lys Met Leu Thr Arg Gly Met Cys Val Glu Leu
                165                 170                 175
Ala Arg His Asn Ile Gln Val Asn Gly Ile Ala Pro Gly Tyr Phe Lys
                180                 185                 190
```

```
Thr Glu Met Thr Lys Ala Leu Val Glu Asp Glu Ala Phe Thr Ala Trp
            195                 200                 205
Leu Cys Lys Arg Thr Pro Ala Ala Arg Trp Gly Asp Pro Gln Glu Leu
        210                 215                 220
Ile Gly Ala Ala Val Phe Leu Ser Ser Lys Ala Ser Asp Phe Val Asn
225                 230                 235                 240
Gly His Leu Leu Phe Val Asp Gly Gly Met Leu Val Ala Val
                245                 250

<210> SEQ ID NO 11
<211> LENGTH: 254
<212> TYPE: PRT
<213> ORGANISM: Artificial
<220> FEATURE:
<223> OTHER INFORMATION: Synthesized: M146I mutation

<400> SEQUENCE: 11

Met Asn Asp Leu Phe Ser Leu Ala Gly Lys Asn Ile Leu Ile Thr Gly
1               5                   10                  15
Ser Ala Gln Gly Ile Gly Phe Leu Leu Ala Thr Gly Leu Gly Lys Tyr
            20                  25                  30
Gly Ala Gln Ile Ile Ile Asn Asp Ile Thr Ala Glu Arg Ala Glu Leu
        35                  40                  45
Ala Val Glu Lys Leu His Gln Glu Gly Ile Gln Val Ala Ala Pro
50                  55                  60
Phe Asn Val Thr His Lys His Glu Ile Asp Ala Ala Val Glu His Ile
65                  70                  75                  80
Glu Lys Asp Ile Gly Pro Ile Asp Val Leu Val Asn Asn Ala Gly Ile
                85                  90                  95
Gln Arg Arg His Pro Phe Thr Glu Phe Pro Glu Gln Glu Trp Asn Asp
            100                 105                 110
Val Ile Ala Val Asn Gln Thr Ala Val Phe Leu Val Ser Gln Ala Val
        115                 120                 125
Thr Arg His Met Val Glu Arg Lys Ala Gly Lys Val Ile Asn Ile Cys
130                 135                 140
Ser Ile Gln Ser Glu Leu Gly Arg Asp Thr Ile Thr Pro Tyr Ala Ala
145                 150                 155                 160
Ser Lys Gly Ala Val Lys Met Leu Thr Arg Gly Met Cys Val Glu Leu
                165                 170                 175
Ala Arg His Asn Ile Gln Val Asn Gly Ile Ala Pro Gly Tyr Phe Lys
            180                 185                 190
Thr Glu Met Thr Lys Ala Leu Val Glu Asp Glu Ala Phe Thr Ala Trp
        195                 200                 205
Leu Cys Lys Arg Thr Pro Ala Ala Arg Trp Gly Asp Pro Gln Glu Leu
    210                 215                 220
Ile Gly Ala Ala Val Phe Leu Ser Ser Lys Ala Ser Asp Phe Val Asn
225                 230                 235                 240
Gly His Leu Leu Phe Val Asp Gly Gly Met Leu Val Ala Val
                245                 250

<210> SEQ ID NO 12
<211> LENGTH: 254
<212> TYPE: PRT
<213> ORGANISM: Artificial
<220> FEATURE:
<223> OTHER INFORMATION: Synthesized: G85C/A120G/V140I mutations

<400> SEQUENCE: 12
```

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Ile
65                  70                  75                  80

Glu Lys Asp Ile Cys Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Gly Val Phe Leu Val Ser Gln Ala Val
            115                 120                 125

Thr Arg His Met Val Glu Arg Lys Ala Gly Lys Ile Ile Asn Ile Cys
130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 13
<211> LENGTH: 254
<212> TYPE: PRT
<213> ORGANISM: Artificial
<220> FEATURE:
<223> OTHER INFORMATION: Synthesized: D237E mutation

<400> SEQUENCE: 13

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110
```

```
Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Glu Met Thr Lys Ala Leu Val Glu Asp Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Glu Phe Val Asn
225                 230                 235                 240

Gly His Leu Leu Phe Val Asp Gly Gly Met Leu Val Ala Val
                245                 250

<210> SEQ ID NO 14
<211> LENGTH: 254
<212> TYPE: PRT
<213> ORGANISM: Artificial
<220> FEATURE:
<223> OTHER INFORMATION: Synthesized: F191I/D220E mutations

<400> SEQUENCE: 14

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Ile Lys
                180                 185                 190

Thr Glu Met Thr Lys Ala Leu Val Glu Asp Ala Phe Thr Ala Trp
        195                 200                 205

Leu Cys Lys Arg Thr Pro Ala Ala Arg Trp Gly Glu Pro Gln Glu Leu
210                 215                 220

Ile Gly Ala Ala Val Phe Leu Ser Ser Lys Ala Ser Asp Phe Val Asn
```

```
                    225                 230                 235                 240

Gly His Leu Leu Phe Val Asp Gly Gly Met Leu Val Ala Val
                245                 250

<210> SEQ ID NO 15
<211> LENGTH: 254
<212> TYPE: PRT
<213> ORGANISM: Artificial
<220> FEATURE:
<223> OTHER INFORMATION: Synthesized: E109D mutation

<400> SEQUENCE: 15

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Asp Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 16
<211> LENGTH: 254
<212> TYPE: PRT
<213> ORGANISM: Artificial
<220> FEATURE:
<223> OTHER INFORMATION: Synthesized: A228G mutation

<400> SEQUENCE: 16

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
```

```
                35                  40                  45
Ala Val Glu Lys Leu His Gln Glu Gly Ile Gln Ala Val Ala Ala Pro
         50                  55                  60

Phe Asn Val Thr His Lys His Glu Ile Asp Ala Ala Val Glu His Ile
 65                  70                  75                  80

Glu Lys Asp Ile Gly Pro Ile Asp Val Leu Val Asn Asn Ala Gly Ile
                 85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Gly Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 17
<211> LENGTH: 254
<212> TYPE: PRT
<213> ORGANISM: Artificial
<220> FEATURE:
<223> OTHER INFORMATION: Synthesized: G30S/H131R mutations

<400> SEQUENCE: 17

Met Asn Asp Leu Phe Ser Leu Ala Gly Lys Asn Ile Leu Ile Thr Gly
 1               5                  10                  15

Ser Ala Gln Gly Ile Gly Phe Leu Leu Ala Thr Gly Leu Ser Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr His Lys His Glu Ile Asp Ala Ala Val Glu His Ile
 65                  70                  75                  80

Glu Lys Asp Ile Gly Pro Ile Asp Val Leu Val Asn Asn Ala Gly Ile
                 85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg Arg Met Val Glu Arg Lys Ala Gly Lys Val Ile Asn Ile Cys
    130                 135                 140

Ser Met Gln Ser Glu Leu Gly Arg Asp Thr Ile Thr Pro Tyr Ala Ala
145                 150                 155                 160
```

```
Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 18
<211> LENGTH: 254
<212> TYPE: PRT
<213> ORGANISM: Artificial
<220> FEATURE:
<223> OTHER INFORMATION: Synthesized: N142I/F191L mutations

<400> SEQUENCE: 18

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Ile Ile Cys
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Leu Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 19
<211> LENGTH: 254
```

```
<212> TYPE: PRT
<213> ORGANISM: Artificial
<220> FEATURE:
<223> OTHER INFORMATION: Synthesized: K82T/P86T/G95A mutations

<400> SEQUENCE: 19

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 20
<211> LENGTH: 254
<212> TYPE: PRT
<213> ORGANISM: Artificial
<220> FEATURE:
<223> OTHER INFORMATION: Synthesized: G95A mutation

<400> SEQUENCE: 20

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80
```

```
Glu Lys Asp Ile Gly Pro Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 21
<211> LENGTH: 254
<212> TYPE: PRT
<213> ORGANISM: Artificial
<220> FEATURE:
<223> OTHER INFORMATION: Synthesized: E194K mutation

<400> SEQUENCE: 21

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Lys Met Thr Lys Ala Leu Val Glu Asp Glu Ala Phe Thr Ala Trp
```

```
                        195                 200                 205
Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 22
<211> LENGTH: 254
<212> TYPE: PRT
<213> ORGANISM: Artificial
<220> FEATURE:
<223> OTHER INFORMATION: Synthesized: G95A/M146I mutations

<400> SEQUENCE: 22

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 23
<211> LENGTH: 254
<212> TYPE: PRT
<213> ORGANISM: Artificial
<220> FEATURE:
<223> OTHER INFORMATION: Synthesized: H69R/K82T/P86T/G95A/M146I
      mutations

<400> SEQUENCE: 23
```

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
50                  55                  60

Phe Asn Val Thr Arg Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
            130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 24
<211> LENGTH: 254
<212> TYPE: PRT
<213> ORGANISM: Artificial
<220> FEATURE:
<223> OTHER INFORMATION: Synthesized: A63V/K82T/P86T/G95A/T154S/D237E
      mutations

<400> SEQUENCE: 24

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Val Pro
50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

-continued

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Met Gln Ser Glu Leu Gly Arg Asp Ser Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Glu Met Thr Lys Ala Leu Val Glu Asp Ala Phe Thr Ala Trp
            195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Glu Phe Val Asn
225                 230                 235                 240

Gly His Leu Leu Phe Val Asp Gly Gly Met Leu Val Ala Val
                245                 250

<210> SEQ ID NO 25
<211> LENGTH: 254
<212> TYPE: PRT
<213> ORGANISM: Artificial
<220> FEATURE:
<223> OTHER INFORMATION: Synthesized: K82T/P86T/G95A/M146I/V200A/V254L
      mutations

<400> SEQUENCE: 25

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Glu Met Thr Lys Ala Leu Ala Glu Asp Glu Ala Phe Thr Ala Trp
            195                 200                 205

Leu Cys Lys Arg Thr Pro Ala Ala Arg Trp Gly Asp Pro Gln Glu Leu
210                 215                 220

```
Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 26
<211> LENGTH: 254
<212> TYPE: PRT
<213> ORGANISM: Artificial
<220> FEATURE:
<223> OTHER INFORMATION: Synthesized: K82T/P86T/G95A/M146I mutations

<400> SEQUENCE: 26

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 27
<211> LENGTH: 254
<212> TYPE: PRT
<213> ORGANISM: Artificial
<220> FEATURE:
<223> OTHER INFORMATION: Synthesized: E51K/G95A/M146I mutations

<400> SEQUENCE: 27

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30
```

```
Gly Ala Gln Ile Ile Ile Asn Asp Ile Thr Ala Glu Arg Ala Glu Leu
            35                  40                  45

Ala Val Lys Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Ala Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 28
<211> LENGTH: 254
<212> TYPE: PRT
<213> ORGANISM: Artificial
<220> FEATURE:
<223> OTHER INFORMATION: Synthesized: T154S/V254L mutations

<400> SEQUENCE: 28

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
130                 135                 140

Ser Met Gln Ser Glu Leu Gly Arg Asp Ser Ile Thr Pro Tyr Ala Ala
```

```
            145                 150                 155                 160
Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 29
<211> LENGTH: 254
<212> TYPE: PRT
<213> ORGANISM: Artificial
<220> FEATURE:
<223> OTHER INFORMATION: Synthesized: T154S/D237E/V254L mutations

<400> SEQUENCE: 29

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Ser Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Glu Phe Val Asn
225                 230                 235                 240

Gly His Leu Leu Phe Val Asp Gly Gly Met Leu Val Ala Leu
                245                 250

<210> SEQ ID NO 30
```

-continued

```
<211> LENGTH: 254
<212> TYPE: PRT
<213> ORGANISM: Artificial
<220> FEATURE:
<223> OTHER INFORMATION: Synthesized: D83E/G95A/V200A/V254L mutations

<400> SEQUENCE: 30

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60
Phe Asn Val Thr His Lys His Glu Ile Asp Ala Ala Val Glu His Ile
65                  70                  75                  80

Glu Lys Glu Ile Gly Pro Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Ala Glu Asp Gly Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 31
<211> LENGTH: 254
<212> TYPE: PRT
<213> ORGANISM: Artificial
<220> FEATURE:
<223> OTHER INFORMATION: Synthesized: C144G/A227T/V254L mutations

<400> SEQUENCE: 31

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80
```

```
Glu Lys Asp Ile Gly Pro Ile Asp Val Leu Val Asn Asn Ala Gly Ile
                 85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Gly
        130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Thr Val Phe Leu Ser Ser Lys Ala Ser Asp Phe Val Asn
225                 230                 235                 240

Gly His Leu Leu Phe Val Asp Gly Gly Met Leu Val Ala Leu
                245                 250
```

<210> SEQ ID NO 32
<211> LENGTH: 254
<212> TYPE: PRT
<213> ORGANISM: Artificial
<220> FEATURE:
<223> OTHER INFORMATION: Synthesized: C144G/V254L mutations

<400> SEQUENCE: 32

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Gly
        130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190
```

```
Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
        210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 33
<211> LENGTH: 254
<212> TYPE: PRT
<213> ORGANISM: Artificial
<220> FEATURE:
<223> OTHER INFORMATION: Synthesized: F23L/C144G/E201D/V254L mutations

<400> SEQUENCE: 33

Met Asn Asp Leu Phe Ser Leu Ala Gly Lys Asn Ile Leu Ile Thr Gly
1               5                   10                  15

Ser Ala Gln Gly Ile Gly Leu Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Gly
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Asp Asp Glu Ala Phe Thr Ala Trp
        195                 200                 205

Leu Cys Lys Arg Thr Pro Ala Ala Arg Trp Gly Asp Pro Gln Glu Leu
        210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 34
<211> LENGTH: 254
<212> TYPE: PRT
<213> ORGANISM: Artificial
<220> FEATURE:
<223> OTHER INFORMATION: Synthesized: F5Y/E51K/C144G/V254L mutations

<400> SEQUENCE: 34
```

Met Asn Asp Leu Tyr Ser Leu Ala Gly Lys Asn Ile Leu Ile Thr Gly
1               5                   10                  15

Ser Ala Gln Gly Ile Gly Phe Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Lys Lys Leu His Gln Glu Gly Ile Gln Ala Val Ala Ala Pro
        50                  55                  60

Phe Asn Val Thr His Lys His Glu Ile Asp Ala Ala Val Glu His Ile
65              70                  75                  80

Glu Lys Asp Ile Gly Pro Ile Asp Val Leu Val Asn Asn Ala Gly Ile
            85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Gly
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Ala Phe Thr Ala Trp
    195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
            245                 250

<210> SEQ ID NO 35
<211> LENGTH: 254
<212> TYPE: PRT
<213> ORGANISM: Artificial
<220> FEATURE:
<223> OTHER INFORMATION: Synthesized: I80F/M146I/V254L mutations

<400> SEQUENCE: 35

Met Asn Asp Leu Phe Ser Leu Ala Gly Lys Asn Ile Leu Ile Thr Gly
1               5                   10                  15

Ser Ala Gln Gly Ile Gly Phe Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr His Lys His Glu Ile Asp Ala Ala Val Glu His Phe
65              70                  75                  80

Glu Lys Asp Ile Gly Pro Ile Asp Val Leu Val Asn Asn Ala Gly Ile
            85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val

```
                    115                 120                 125
Thr Arg His Met Val Glu Arg Lys Ala Gly Lys Val Ile Asn Ile Cys
130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 36
<211> LENGTH: 254
<212> TYPE: PRT
<213> ORGANISM: Artificial
<220> FEATURE:
<223> OTHER INFORMATION: Synthesized: A63V/V241I/Q222H mutations

<400> SEQUENCE: 36

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Val Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Ile Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro His Glu Leu
    210                 215                 220

Ile Gly Ala Ala Val Phe Leu Ser Ser Lys Ala Ser Asp Phe Val Asn
225                 230                 235                 240
```

Gly His Leu Leu Phe Val Asp Gly Gly Met Leu Val Ala Val
            245                 250

<210> SEQ ID NO 37
<211> LENGTH: 254
<212> TYPE: PRT
<213> ORGANISM: Artificial
<220> FEATURE:
<223> OTHER INFORMATION: Synthesized: K136M/C144G/E175K/V254L mutations

<400> SEQUENCE: 37

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Gln Glu Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Met Ala Gly Lys Val Ile Asn Ile Gly
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Lys Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
            245                 250

<210> SEQ ID NO 38
<211> LENGTH: 254
<212> TYPE: PRT
<213> ORGANISM: Artificial
<220> FEATURE:
<223> OTHER INFORMATION: Synthesized: C131R/C144G/S148G/V254L mutations

<400> SEQUENCE: 38

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

```
Ala Val Glu Lys Leu His Gln Glu Gly Ile Gln Ala Val Ala Ala Pro
             50                  55                  60

Phe Asn Val Thr His Lys His Glu Ile Asp Ala Ala Val Glu His Ile
 65                  70                  75                  80

Glu Lys Asp Ile Gly Pro Ile Asp Val Leu Val Asn Asn Ala Gly Ile
                 85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg Arg Met Val Glu Arg Lys Ala Gly Lys Val Ile Asn Ile Gly
130                 135                 140

Ser Met Gln Gly Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 39
<211> LENGTH: 254
<212> TYPE: PRT
<213> ORGANISM: Artificial
<220> FEATURE:
<223> OTHER INFORMATION: Synthesized: A63V/R99C mutations

<400> SEQUENCE: 39

Met Asn Asp Leu Phe Ser Leu Ala Gly Lys Asn Ile Leu Ile Thr Gly
 1               5                  10                  15

Ser Ala Gln Gly Ile Gly Phe Leu Leu Ala Thr Gly Leu Gly Lys Tyr
             20                  25                  30

Gly Ala Gln Ile Ile Ile Asn Asp Ile Thr Ala Glu Arg Ala Glu Leu
         35                  40                  45

Ala Val Glu Lys Leu His Gln Glu Gly Ile Gln Ala Val Ala Val Pro
             50                  55                  60

Phe Asn Val Thr His Lys His Glu Ile Asp Ala Ala Val Glu His Ile
 65                  70                  75                  80

Glu Lys Asp Ile Gly Pro Ile Asp Val Leu Val Asn Asn Ala Gly Ile
                 85                  90                  95

Gln Arg Cys His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Ile Thr Pro Tyr Ala Ala
145                 150                 155                 160
```

Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
            245                 250

<210> SEQ ID NO 40
<211> LENGTH: 254
<212> TYPE: PRT
<213> ORGANISM: Artificial
<220> FEATURE:
<223> OTHER INFORMATION: Synthesized: L24I/I80F/M146I mutations

<400> SEQUENCE: 40

Met Asn Asp Leu Phe Ser Leu Ala Gly Lys Asn Ile Leu Ile Thr Gly
1               5                   10                  15

Ser Ala Gln Gly Ile Gly Phe Ile Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Phe
65                  70                  75                  80

Glu Lys Asp Ile Gly Pro Ile Asp Val Leu Val Asn Asn Ala Gly Ile
            85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
            130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
            245                 250

<210> SEQ ID NO 41
<211> LENGTH: 254
<212> TYPE: PRT

-continued

```
<213> ORGANISM: Artificial
<220> FEATURE:
<223> OTHER INFORMATION: Synthesized: H54R/A63V/E201V/V254L mutations

<400> SEQUENCE: 41
```

| | | | | | | | | | | | | | | |
|---|---|---|---|---|---|---|---|---|---|---|---|---|---|---|
| Met | Asn | Asp | Leu | Phe | Ser | Leu | Ala | Gly | Lys | Asn | Ile | Leu | Ile | Thr | Gly |
| 1 | | | | 5 | | | | | 10 | | | | | 15 | |

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu Arg Gln Glu Gly Ile Gln Ala Val Ala Val Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Val Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

```
<210> SEQ ID NO 42
<211> LENGTH: 254
<212> TYPE: PRT
<213> ORGANISM: Artificial
<220> FEATURE:
<223> OTHER INFORMATION: Synthesized: H54L/H100Y/C144G/V254L mutations

<400> SEQUENCE: 42
```

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu Leu Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile

Gln Arg Arg Tyr Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Gly
        130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 43
<211> LENGTH: 254
<212> TYPE: PRT
<213> ORGANISM: Artificial
<220> FEATURE:
<223> OTHER INFORMATION: Synthesized: Q59E/K82T/P86T/G95A/T154S/V254L
      mutations

<400> SEQUENCE: 43

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Glu Ala Val Ala Ala Pro
50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Met Gln Ser Glu Leu Gly Arg Asp Ser Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp 195                 200                 205
Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 44
<211> LENGTH: 254
<212> TYPE: PRT
<213> ORGANISM: Artificial
<220> FEATURE:
<223> OTHER INFORMATION: Synthesized: E72V/I155T/V254L mutations

<400> SEQUENCE: 44

Met Asn Asp Leu Phe Ser Leu Ala Gly Lys Asn Ile Leu Ile Thr Gly
1               5                   10                  15

Ser Ala Gln Gly Ile Gly Phe Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
50                  55                  60

Phe Asn Val Thr His Lys His Val Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 45
<211> LENGTH: 254
<212> TYPE: PRT
<213> ORGANISM: Artificial
<220> FEATURE:
<223> OTHER INFORMATION: Synthesized: A63V/I155T mutations

<400> SEQUENCE: 45

Met Asn Asp Leu Phe Ser Leu Ala Gly Lys Asn Ile Leu Ile Thr Gly

```
                1               5                   10                  15
Ser Ala Gln Gly Ile Gly Phe Leu Leu Ala Thr Gly Leu Gly Lys Tyr
                20                  25                  30
Gly Ala Gln Ile Ile Ile Asn Asp Ile Thr Ala Glu Arg Ala Glu Leu
                35                  40                  45
Ala Val Glu Lys Leu His Gln Glu Gly Ile Gln Ala Val Ala Val Pro
            50                  55                  60
Phe Asn Val Thr His Lys His Glu Ile Asp Ala Val Glu His Ile
65                  70                  75                  80
Glu Lys Asp Ile Gly Pro Ile Asp Val Leu Val Asn Asn Ala Gly Ile
                    85                  90                  95
Gln Arg Arg His Pro Phe Thr Glu Phe Pro Glu Gln Glu Trp Asn Asp
                100                 105                 110
Val Ile Ala Val Asn Gln Thr Ala Val Phe Leu Val Ser Gln Ala Val
                115                 120                 125
Thr Arg His Met Val Glu Arg Lys Ala Gly Lys Val Ile Asn Ile Cys
            130                 135                 140
Ser Met Gln Ser Glu Leu Gly Arg Asp Thr Thr Thr Pro Tyr Ala Ala
145                 150                 155                 160
Ser Lys Gly Ala Val Lys Met Leu Thr Arg Gly Met Cys Val Glu Leu
                    165                 170                 175
Ala Arg His Asn Ile Gln Val Asn Gly Ile Ala Pro Gly Tyr Phe Lys
                180                 185                 190
Thr Glu Met Thr Lys Ala Leu Val Glu Asp Glu Ala Phe Thr Ala Trp
            195                 200                 205
Leu Cys Lys Arg Thr Pro Ala Ala Arg Trp Gly Asp Pro Gln Glu Leu
            210                 215                 220
Ile Gly Ala Ala Val Phe Leu Ser Ser Lys Ala Ser Asp Phe Val Asn
225                 230                 235                 240
Gly His Leu Leu Phe Val Asp Gly Gly Met Leu Val Ala Val
                    245                 250

<210> SEQ ID NO 46
<211> LENGTH: 254
<212> TYPE: PRT
<213> ORGANISM: Artificial
<220> FEATURE:
<223> OTHER INFORMATION: Synthesized: K82T/P86T/G95A/I155T/V254L
      mutations

<400> SEQUENCE: 46

Met Asn Asp Leu Phe Ser Leu Ala Gly Lys Asn Ile Leu Ile Thr Gly
1               5                   10                  15
Ser Ala Gln Gly Ile Gly Phe Leu Leu Ala Thr Gly Leu Gly Lys Tyr
                20                  25                  30
Gly Ala Gln Ile Ile Ile Asn Asp Ile Thr Ala Glu Arg Ala Glu Leu
                35                  40                  45
Ala Val Glu Lys Leu His Gln Glu Gly Ile Gln Ala Val Ala Ala Pro
            50                  55                  60
Phe Asn Val Thr His Lys His Glu Ile Asp Ala Ala Val Glu His Ile
65                  70                  75                  80
Glu Thr Asp Ile Gly Thr Ile Asp Val Leu Val Asn Asn Ala Ala Ile
                    85                  90                  95
Gln Arg Arg His Pro Phe Thr Glu Phe Pro Glu Gln Glu Trp Asn Asp
                100                 105                 110
Val Ile Ala Val Asn Gln Thr Ala Val Phe Leu Val Ser Gln Ala Val
```

```
            115                 120                 125
Thr Arg His Met Val Glu Arg Lys Ala Gly Lys Val Ile Asn Ile Cys
130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 47
<211> LENGTH: 254
<212> TYPE: PRT
<213> ORGANISM: Artificial
<220> FEATURE:
<223> OTHER INFORMATION: Synthesized: F5Y/E51K/I155T/V254L mutations

<400> SEQUENCE: 47

Met Asn Asp Leu Tyr Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Lys Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240
```

```
Gly His Leu Leu Phe Val Asp Gly Gly Met Leu Val Ala Leu
            245                 250
```

<210> SEQ ID NO 48
<211> LENGTH: 254
<212> TYPE: PRT
<213> ORGANISM: Artificial
<220> FEATURE:
<223> OTHER INFORMATION: Synthesized: E51K/I155T/V254L mutations

<400> SEQUENCE: 48

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Lys Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250
```

<210> SEQ ID NO 49
<211> LENGTH: 254
<212> TYPE: PRT
<213> ORGANISM: Artificial
<220> FEATURE:
<223> OTHER INFORMATION: Synthesized: I155T/E194G mutations

<400> SEQUENCE: 49

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45
```

```
Ala Val Glu Lys Leu His Gln Glu Gly Ile Gln Ala Val Ala Pro
 50                  55                  60

Phe Asn Val Thr His Lys His Glu Ile Asp Ala Ala Val Glu His Ile
 65                  70                  75                  80

Glu Lys Asp Ile Gly Pro Ile Asp Val Leu Val Asn Asn Ala Gly Ile
                 85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
                115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Gly Met Thr Lys Ala Leu Val Glu Asp Glu Ala Phe Thr Ala Trp
                195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 50
<211> LENGTH: 254
<212> TYPE: PRT
<213> ORGANISM: Artificial
<220> FEATURE:
<223> OTHER INFORMATION: Synthesized: A63V/V124I/M146I mutations

<400> SEQUENCE: 50

Met Asn Asp Leu Phe Ser Leu Ala Gly Lys Asn Ile Leu Ile Thr Gly
 1               5                  10                  15

Ser Ala Gln Gly Ile Gly Phe Leu Leu Ala Thr Gly Leu Gly Lys Tyr
                 20                  25                  30

Gly Ala Gln Ile Ile Ile Asn Asp Ile Thr Ala Glu Arg Ala Glu Leu
             35                  40                  45

Ala Val Glu Lys Leu His Gln Glu Gly Ile Gln Ala Val Ala Val Pro
 50                  55                  60

Phe Asn Val Thr His Lys His Glu Ile Asp Ala Ala Val Glu His Ile
 65                  70                  75                  80

Glu Lys Asp Ile Gly Pro Ile Asp Val Leu Val Asn Asn Ala Gly Ile
                 85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Ile Ser Gln Ala Val
                115                 120                 125

Thr Arg His Met Val Glu Arg Lys Ala Gly Lys Val Ile Asn Ile Cys
130                 135                 140

Ser Ile Gln Ser Glu Leu Gly Arg Asp Thr Ile Thr Pro Tyr Ala Ala
145                 150                 155                 160
```

```
Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
            245                 250

<210> SEQ ID NO 51
<211> LENGTH: 254
<212> TYPE: PRT
<213> ORGANISM: Artificial
<220> FEATURE:
<223> OTHER INFORMATION: Synthesized: D3H/G57D/M146I/V254L mutations

<400> SEQUENCE: 51

Met Asn His Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Asp Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 52
<211> LENGTH: 254
<212> TYPE: PRT
```

-continued

```
<213> ORGANISM: Artificial
<220> FEATURE:
<223> OTHER INFORMATION: Synthesized: G95A/I155T/V254L mutations

<400> SEQUENCE: 52
```

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

```
<210> SEQ ID NO 53
<211> LENGTH: 254
<212> TYPE: PRT
<213> ORGANISM: Artificial
<220> FEATURE:
<223> OTHER INFORMATION: Synthesized: I155T/F230L mutations

<400> SEQUENCE: 53
```

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile

```
                      85                   90                   95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Leu Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 54
<211> LENGTH: 254
<212> TYPE: PRT
<213> ORGANISM: Artificial
<220> FEATURE:
<223> OTHER INFORMATION: Synthesized: I155T/I225T/V254L mutations

<400> SEQUENCE: 54

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205
```

```
Leu Cys Lys Arg Thr Pro Ala Ala Arg Trp Gly Asp Pro Gln Glu Leu
        210                 215                 220

Thr Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 55
<211> LENGTH: 254
<212> TYPE: PRT
<213> ORGANISM: Artificial
<220> FEATURE:
<223> OTHER INFORMATION: Synthesized: T103I/M146I mutations

<400> SEQUENCE: 55

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Pro
        50                  55                  60

Phe Asn Val Thr His Lys His Glu Ile Asp Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Ile Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 56
<211> LENGTH: 254
<212> TYPE: PRT
<213> ORGANISM: Artificial
<220> FEATURE:
<223> OTHER INFORMATION: Synthesized: G28D/H69A/G95A/E194G/V254L
      mutations

<400> SEQUENCE: 56

Met Asn Asp Leu Phe Ser Leu Ala Gly Lys Asn Ile Leu Ile Thr Gly
```

```
                 1               5                  10                 15
Ser Ala Gln Gly Ile Gly Phe Leu Leu Ala Thr Asp Leu Gly Lys Tyr
                20                  25                 30

Gly Ala Gln Ile Ile Ile Asn Asp Ile Thr Ala Glu Arg Ala Glu Leu
                35                  40                 45

Ala Val Glu Lys Leu His Gln Glu Gly Ile Gln Ala Val Ala Ala Pro
                50                  55                 60

Phe Asn Val Thr Ala Lys His Glu Ile Asp Ala Val Glu His Ile
 65                  70                  75                 80

Glu Lys Asp Ile Gly Pro Ile Asp Val Leu Val Asn Asn Ala Ala Ile
                85                  90                 95

Gln Arg Arg His Pro Phe Thr Glu Phe Pro Glu Gln Glu Trp Asn Asp
                100                 105                110

Val Ile Ala Val Asn Gln Thr Ala Val Phe Leu Val Ser Gln Ala Val
                115                 120                125

Thr Arg His Met Val Glu Arg Lys Ala Gly Lys Val Ile Asn Ile Cys
                130                 135                140

Ser Met Gln Ser Glu Leu Gly Arg Asp Thr Ile Thr Pro Tyr Ala Ala
145                 150                 155                160

Ser Lys Gly Ala Val Lys Met Leu Thr Arg Gly Met Cys Val Glu Leu
                165                 170                175

Ala Arg His Asn Ile Gln Val Asn Gly Ile Ala Pro Gly Tyr Phe Lys
                180                 185                190

Thr Gly Met Thr Lys Ala Leu Val Glu Asp Glu Ala Phe Thr Ala Trp
                195                 200                205

Leu Cys Lys Arg Thr Pro Ala Ala Arg Trp Gly Asp Pro Gln Glu Leu
                210                 215                220

Ile Gly Ala Ala Val Phe Leu Ser Ser Lys Ala Ser Asp Phe Val Asn
225                 230                 235                240

Gly His Leu Leu Phe Val Asp Gly Gly Met Leu Val Ala Leu
                245                 250

<210> SEQ ID NO 57
<211> LENGTH: 254
<212> TYPE: PRT
<213> ORGANISM: Artificial
<220> FEATURE:
<223> OTHER INFORMATION: Synthesized: L24I/E47K/E51K/I155T/Y190F/E203K
      mutations

<400> SEQUENCE: 57

Met Asn Asp Leu Phe Ser Leu Ala Gly Lys Asn Ile Leu Ile Thr Gly
 1               5                  10                 15

Ser Ala Gln Gly Ile Gly Phe Ile Leu Ala Thr Gly Leu Gly Lys Tyr
                20                  25                 30

Gly Ala Gln Ile Ile Ile Asn Asp Ile Thr Ala Glu Arg Ala Lys Leu
                35                  40                 45

Ala Val Lys Lys Leu His Gln Glu Gly Ile Gln Ala Val Ala Ala Pro
                50                  55                 60

Phe Asn Val Thr His Lys His Glu Ile Asp Ala Val Glu His Ile
 65                  70                  75                 80

Glu Lys Asp Ile Gly Pro Ile Asp Val Leu Val Asn Asn Ala Gly Ile
                85                  90                 95

Gln Arg Arg His Pro Phe Thr Glu Phe Pro Glu Gln Glu Trp Asn Asp
                100                 105                110

Val Ile Ala Val Asn Gln Thr Ala Val Phe Leu Val Ser Gln Ala Val
```

```
                    115                 120                 125
Thr Arg His Met Val Glu Arg Lys Ala Gly Lys Val Ile Asn Ile Cys
130                     135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                    165                 170                 175

Ala Arg His Asn Ile Gln Val Asn Gly Ile Ala Pro Gly Phe Phe Lys
                180                 185                 190

Thr Glu Met Thr Lys Ala Leu Val Glu Asp Lys Ala Phe Thr Ala Trp
            195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250
```

<210> SEQ ID NO 58
<211> LENGTH: 254
<212> TYPE: PRT
<213> ORGANISM: Artificial
<220> FEATURE:
<223> OTHER INFORMATION: Synthesized: I58F/C144G/E194G mutations

<400> SEQUENCE: 58

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Phe Gln Ala Val Ala Ala Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Gly
130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Gly Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240
```

Gly His Leu Leu Phe Val Asp Gly Gly Met Leu Val Ala Val
            245                 250

<210> SEQ ID NO 59
<211> LENGTH: 254
<212> TYPE: PRT
<213> ORGANISM: Artificial
<220> FEATURE:
<223> OTHER INFORMATION: Synthesized: F65Y/M146I/I155T/V254L mutations

<400> SEQUENCE: 59

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Tyr Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Ile Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
            245                 250

<210> SEQ ID NO 60
<211> LENGTH: 254
<212> TYPE: PRT
<213> ORGANISM: Artificial
<220> FEATURE:
<223> OTHER INFORMATION: Synthesized: A63V/M146I mutations

<400> SEQUENCE: 60

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

```
Ala Val Glu Lys Leu His Gln Glu Gly Ile Gln Ala Val Ala Val Pro
         50                  55                  60

Phe Asn Val Thr His Lys His Glu Ile Asp Ala Ala Val Glu His Ile
 65                  70                  75                  80

Glu Lys Asp Ile Gly Pro Ile Asp Val Leu Val Asn Asn Ala Gly Ile
                 85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 61
<211> LENGTH: 254
<212> TYPE: PRT
<213> ORGANISM: Artificial
<220> FEATURE:
<223> OTHER INFORMATION: Synthesized: G9R/E56G/A63V/M146I/D237N
      mutations

<400> SEQUENCE: 61

Met Asn Asp Leu Phe Ser Leu Ala Arg Lys Asn Ile Leu Ile Thr Gly
 1               5                  10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Gly Gly Ile Gln Ala Val Ala Val Pro
         50                  55                  60

Phe Asn Val Thr His Lys His Glu Ile Asp Ala Ala Val Glu His Ile
 65                  70                  75                  80

Glu Lys Asp Ile Gly Pro Ile Asp Val Leu Val Asn Asn Ala Gly Ile
                 85                  90                  95

Gln Arg Arg His Pro Phe Thr Glu Phe Pro Gln Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Ile Gln Ser Glu Leu Gly Arg Asp Thr Ile Thr Pro Tyr Ala Ala
145                 150                 155                 160
```

```
Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asn Phe Val Asn
225                 230                 235                 240

Gly His Leu Leu Phe Val Asp Gly Gly Met Leu Val Ala Val
                245                 250

<210> SEQ ID NO 62
<211> LENGTH: 254
<212> TYPE: PRT
<213> ORGANISM: Artificial
<220> FEATURE:
<223> OTHER INFORMATION: Synthesized: V61I/H69R/M146I mutations

<400> SEQUENCE: 62

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Ile Ala Ala Pro
        50                  55                  60

Phe Asn Val Thr His Lys His Glu Ile Asp Ala Ala Val Glu Arg Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 63
<211> LENGTH: 254
```

-continued

<212> TYPE: PRT
<213> ORGANISM: Artificial
<220> FEATURE:
<223> OTHER INFORMATION: Synthesized: I80F/M146I/I155T mutations

<400> SEQUENCE: 63

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Phe
65                  70                  75                  80

Glu Lys Asp Ile Gly Pro Ile Asp Val Leu Val Asn Asn Ala Gly Ile
            85                  90                  95

Gln Arg Arg His Pro Phe Thr Glu Phe Pro Glu Gln Glu Trp Asn Asp
        100                 105                 110

Val Ile Ala Val Asn Gln Thr Ala Val Phe Leu Val Ser Gln Ala Val
    115                 120                 125

Thr Arg His Met Val Glu Arg Lys Ala Gly Lys Val Ile Asn Ile Cys
130                 135                 140

Ser Ile Gln Ser Glu Leu Gly Arg Asp Thr Leu Thr Pro Tyr Ala Ala
145                 150                 155                 160

Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
        180                 185                 190

Thr Glu Met Thr Lys Ala Leu Val Glu Asp Glu Ala Phe Thr Ala Trp
    195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
            245                 250
```

<210> SEQ ID NO 64
<211> LENGTH: 254
<212> TYPE: PRT
<213> ORGANISM: Artificial
<220> FEATURE:
<223> OTHER INFORMATION: Synthesized: G95A/C144G/V254L mutations

<400> SEQUENCE: 64

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Ile
65                  70                  75                  80
```

Glu Lys Asp Ile Gly Pro Ile Asp Val Leu Val Asn Asn Ala Ala Ile
            85                  90                  95

Gln Arg Arg His Pro Phe Thr Glu Phe Pro Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Gly
            130                 135                 140

Ser Met Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
            245                 250

<210> SEQ ID NO 65
<211> LENGTH: 254
<212> TYPE: PRT
<213> ORGANISM: Artificial
<220> FEATURE:
<223> OTHER INFORMATION: Synthesized: A63T/I155T mutations

<400> SEQUENCE: 65

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Thr Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
            85                  90                  95

Gln Arg Arg His Pro Phe Thr Glu Phe Pro Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
            130                 135                 140

Ser Met Gln Ser Glu Leu Gly Arg Asp Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp

```
                    195                 200                 205
Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 66
<211> LENGTH: 254
<212> TYPE: PRT
<213> ORGANISM: Artificial
<220> FEATURE:
<223> OTHER INFORMATION: Synthesized: A63V/V124I/Q147H mutations

<400> SEQUENCE: 66

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Val Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Ile Ser Gln Ala Val
        115                 120                 125

Thr Arg His Met Val Glu Arg Lys Ala Gly Lys Val Ile Asn Ile Cys
    130                 135                 140

Ser Met His Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250

<210> SEQ ID NO 67
<211> LENGTH: 765
<212> TYPE: DNA
<213> ORGANISM: Escherichia coli

<400> SEQUENCE: 67
atgaacgatc tattttcact ggcaggaaaa aatatcttga ttaccggttc agcacagggc    60
attggctttt tactggcaac cggcctgggt aaatatggcg cacaaataat tattaatgat   120
```

-continued

```
attactgccg aacgcgcaga acttgctgta gaaaaactcc accaggaggg tattcaggcc    180
gttgccgcac cttttaatgt tactcataaa catgaaattg atgccgccgt tgaacatatc    240
gaaaaggaca tcggcccat tgatgtgctg gtgaataacg ccggtatcca gcgccgtcat     300
ccttttactg agttccctga acaagagtgg aatgatgtga tcgcagtaaa ccagaccgcc    360
gtgttcctgg tatcgcaagc ggtaactcgt cacatggttg aacgcaaggc aggtaaagtt    420
attaatattt gctcgatgca aagcgaactg gacgtgaca ccatcacccc ttatgccgca     480
tcgaaagggg cggtaaaaat gctcacccgc ggcatgtgcg tcgagctggc gcgccacaat    540
attcaggtca acggtattgc gccgggctat ttcaaaacag aaatgactaa agcactggtt    600
gaggacgaag ccttcaccgc ctggttgtgc aaacggaccc ccgccgcacg ctggggagat    660
ccgcaggaac tgattggtgc tgcggtgttc ctttcttcaa aagcctctga tttcgtaaac    720
ggccacctgt tgtttgttga tggcggcatg ttagtggctg tttaa                   765
```

<210> SEQ ID NO 68
<211> LENGTH: 31
<212> TYPE: DNA
<213> ORGANISM: Escherichia coli

<400> SEQUENCE: 68

```
ggaattccat atgaacgatc tattttcact g                                   31
```

<210> SEQ ID NO 69
<211> LENGTH: 28
<212> TYPE: DNA
<213> ORGANISM: Escherichia coli

<400> SEQUENCE: 69

```
gcggatcctt aaacagccac taacatgc                                       28
```

<210> SEQ ID NO 70
<211> LENGTH: 254
<212> TYPE: PRT
<213> ORGANISM: Escherichia coli

<400> SEQUENCE: 70

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr Arg Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Gln Asp Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Ile Gln Ser Glu Leu Gly Arg Asp Thr Ile Thr Pro Tyr Ala Ala
145                 150                 155                 160
```

```
Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
            245                 250

<210> SEQ ID NO 71
<211> LENGTH: 254
<212> TYPE: PRT
<213> ORGANISM: Escherichia coli

<400> SEQUENCE: 71

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr Arg Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Ile Gln Ser Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
            245                 250

<210> SEQ ID NO 72
<211> LENGTH: 254
<212> TYPE: PRT
<213> ORGANISM: Escherichia coli
```

<400> SEQUENCE: 72

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Val Pro
50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg Arg Met Val Glu Arg Lys Ala Gly Lys Val Ile Asn Ile Gly
130                 135                 140

Ser Met Gln Cys Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250
```

<210> SEQ ID NO 73
<211> LENGTH: 254
<212> TYPE: PRT
<213> ORGANISM: Escherichia coli

<400> SEQUENCE: 73

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110
```

```
Val Ile Ala Val Asn Gln Thr Ala Val Phe Leu Val Ser Gln Ala Val
            115                 120                 125

Thr Arg Arg Met Val Glu Arg Lys Ala Gly Lys Val Ile Asn Ile Gly
        130                 135                 140

Ser Met Gln Cys Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Glu Met Thr Lys Ala Leu Val Glu Asp Val Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250
```

<210> SEQ ID NO 74
<211> LENGTH: 254
<212> TYPE: PRT
<213> ORGANISM: Escherichia coli

<400> SEQUENCE: 74

```
Met Asn Asp Leu Phe Ser Leu Ala Gly Lys Asn Val Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Leu Ala Lys Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Gly Arg Lys Ala Gly Lys Val Ile Asn Ile Cys
        130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240
```

Gly His Leu Leu Phe Val Asp Gly Gly Met Leu Val Ala Leu
            245                 250

<210> SEQ ID NO 75
<211> LENGTH: 254
<212> TYPE: PRT
<213> ORGANISM: Escherichia coli

<400> SEQUENCE: 75

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg Arg Met Val Glu Arg Lys Ala Gly Lys Val Ile Asn Ile Gly
    130                 135                 140

Ser Met Gln Cys Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
            245                 250

<210> SEQ ID NO 76
<211> LENGTH: 254
<212> TYPE: PRT
<213> ORGANISM: Escherichia coli

<400> SEQUENCE: 76

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile

```
                65                  70                  75                  80
Glu Thr Asp Ile Gly Thr Ile Asp Val Leu Val Asn Asn Ala Ala Ile
                    85                  90                  95
Gln Arg Arg His Pro Phe Thr Glu Phe Pro Glu Gln Glu Trp Asn Asp
                100                 105                 110
Val Ile Ala Val Asn Gln Thr Ala Val Phe Leu Val Ser Gln Ala Val
                115                 120                 125
Thr Arg His Met Val Glu Arg Lys Ala Gly Lys Val Ile Asn Ile Cys
            130                 135                 140
Ser Met Gln Ser Glu Leu Gly Arg Asp Thr Thr Pro Tyr Ala Ala
145                 150                 155                 160
Ser Lys Arg Ala Val Lys Met Leu Thr Arg Gly Met Cys Val Glu Leu
                165                 170                 175
Ala Arg His Asn Ile Gln Val Asn Gly Ile Ala Pro Gly Tyr Ile Lys
            180                 185                 190
Thr Glu Met Thr Lys Ala Leu Val Glu Asp Glu Ala Phe Thr Ala Trp
                195                 200                 205
Leu Cys Lys Arg Thr Pro Ala Ala Arg Trp Gly Asp Pro Gln Glu Leu
            210                 215                 220
Ile Gly Ala Ala Val Phe Leu Ser Ser Lys Ala Ser Asp Phe Val Asn
225                 230                 235                 240
Gly His Leu Leu Phe Val Asp Gly Gly Met Leu Val Ala Leu
                245                 250

<210> SEQ ID NO 77
<211> LENGTH: 254
<212> TYPE: PRT
<213> ORGANISM: Escherichia coli

<400> SEQUENCE: 77

Met Asn Asp Leu Phe Ser Leu Ala Gly Lys Asn Ile Leu Ile Thr Gly
1               5                   10                  15
Ser Ala Gln Gly Ile Gly Phe Leu Leu Ala Thr Gly Leu Gly Lys Tyr
                20                  25                  30
Gly Ala Gln Ile Ile Ile Asn Asp Ile Thr Ala Glu Arg Ala Glu Leu
            35                  40                  45
Ala Val Glu Lys Leu His Gln Glu Gly Ile Gln Ala Val Ala Val Pro
        50                  55                  60
Phe Asn Val Thr His Lys His Glu Ile Asp Ala Ala Val Glu His Ile
65                  70                  75                  80
Glu Thr Asp Ile Gly Thr Ile Asp Val Leu Val Asn Asn Ala Ala Ile
                    85                  90                  95
Gln Arg Arg His Pro Phe Thr Glu Phe Pro Glu Gln Glu Trp Asn Asp
                100                 105                 110
Val Ile Ala Val Asn Gln Thr Ala Val Phe Leu Val Ser Gln Ala Val
                115                 120                 125
Thr Arg Arg Met Val Glu Arg Lys Ala Gly Lys Val Ile Asn Ile Gly
            130                 135                 140
Ser Met Gln Cys Glu Leu Gly Arg Asp Thr Ile Thr Pro Tyr Ala Ala
145                 150                 155                 160
Ser Lys Gly Ala Val Lys Met Leu Thr Arg Gly Met Cys Val Glu Leu
                165                 170                 175
Ala Arg His Asn Ile Gln Val Asn Gly Ile Ala Pro Gly Tyr Phe Lys
            180                 185                 190
Thr Glu Met Thr Lys Ala Leu Val Glu Asp Glu Ala Phe Thr Ala Trp
```

-continued

```
                195                 200                 205
Leu Cys Lys Arg Thr Pro Ala Ala Arg Trp Gly Asp Pro Gln Glu Leu
210                 215                 220

Ile Gly Ala Ala Val Phe Leu Ser Ser Arg Ala Ser Asp Phe Val Asn
225                 230                 235                 240

Gly His Leu Leu Phe Val Asp Leu Gly Met Leu Val Ala Leu
                245                 250

<210> SEQ ID NO 78
<211> LENGTH: 254
<212> TYPE: PRT
<213> ORGANISM: Escherichia coli

<400> SEQUENCE: 78

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
    50                  55                  60

Phe Asn Val Thr Arg Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Leu Leu Val Ala Leu
                245                 250

<210> SEQ ID NO 79
<211> LENGTH: 254
<212> TYPE: PRT
<213> ORGANISM: Escherichia coli

<400> SEQUENCE: 79

Met Asn Asp Leu Phe Ser Leu Ala Gly Lys Asn Ile Leu Ile Thr Gly
1               5                   10                  15

Ser Ala Gln Gly Ile Gly Phe Leu Met Ala Thr Gly Leu Gly Lys Tyr
                20                  25                  30
```

Gly Ala Gln Ile Ile Ile Asn Asp Ile Thr Ala Glu Arg Ala Glu Leu
                35                  40                  45

Ala Val Glu Lys Leu His Gln Glu Gly Ile Gln Ala Val Ala Ala Pro
 50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
                115                 120                 125

Thr Arg His Met Val Glu Arg Lys Ala Gly Lys Val Ile Asn Ile Cys
                130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Glu Met Thr Lys Ala Leu Val Glu Asp Glu Ala Phe Thr Ala Trp
                195                 200                 205

Leu Cys Lys Arg Thr Pro Ala Ala Arg Trp Gly Asp Pro Gln Glu Leu
                210                 215                 220

Ile Gly Ala Ala Val Phe Leu Ser Ser Thr Ala Ser Asp Phe Val Asn
225                 230                 235                 240

Gly His Leu Leu Phe Val Asp Gly Gly Met Leu Val Ala Leu
                245                 250

<210> SEQ ID NO 80
<211> LENGTH: 254
<212> TYPE: PRT
<213> ORGANISM: Escherichia coli

<400> SEQUENCE: 80

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Leu Ile Ile Ile Asn Asp Ile Thr Ala Glu Arg Ala Glu Leu
                35                  40                  45

Ala Val Glu Lys Leu His Gln Glu Gly Ile Gln Ala Val Ala Ala Pro
 50                  55                  60

Phe Asn Val Thr Arg Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Gln Glu Trp Asn Asp
                100                 105                 110

Val Ile Ala Val Asn Gln Thr Gly Val Phe Leu Val Ser Gln Ala Val
                115                 120                 125

Thr Arg His Met Val Glu Arg Lys Ala Gly Lys Val Ile Asn Ile Cys
                130                 135                 140

Ser Ile Gln Ser Glu Leu Gly Arg Asp Thr Ile Thr Pro Tyr Ala Ala
145                 150                 155                 160

```
Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Leu Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 81
<211> LENGTH: 254
<212> TYPE: PRT
<213> ORGANISM: Escherichia coli

<400> SEQUENCE: 81

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly His Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg Arg Met Val Glu Arg Lys Ala Gly Lys Val Ile Asn Ile Gly
    130                 135                 140

Ser Met Gln Cys Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 82
<211> LENGTH: 254
<212> TYPE: PRT
<213> ORGANISM: Escherichia coli
```

<400> SEQUENCE: 82

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Val Pro
50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Glu
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250
```

<210> SEQ ID NO 83
<211> LENGTH: 254
<212> TYPE: PRT
<213> ORGANISM: Escherichia coli

<400> SEQUENCE: 83

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
50                  55                  60

Phe Asn Val Thr Arg Lys His Glu Ile Asp Ala Ala Val Glu His Ile
65                  70                  75                  80

Glu Thr Asp Ile Gly Thr Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110
```

```
Val Ile Ala Val Asn Gln Thr Ala Val Phe Leu Val Ser Gln Ala Val
        115                 120                 125

Thr Arg Arg Met Val Glu Arg Lys Ala Gly Lys Val Ile Asn Ile Gly
130                 135                 140

Ser Met Gln Cys Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250
```

```
<210> SEQ ID NO 84
<211> LENGTH: 254
<212> TYPE: PRT
<213> ORGANISM: Escherichia coli

<400> SEQUENCE: 84

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Asp Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240
```

Gly His Leu Leu Phe Val Asp Gly Gly Met Leu Val Ala Leu
            245                 250

<210> SEQ ID NO 85
<211> LENGTH: 254
<212> TYPE: PRT
<213> ORGANISM: Escherichia coli

<400> SEQUENCE: 85

Met Asn Asp Leu Phe Ser Leu Ala Gly Lys Asn Ile Leu Ile Thr Gly
1               5                   10                  15

Ser Ala Gln Gly Ile Gly Phe Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
            245                 250

<210> SEQ ID NO 86
<211> LENGTH: 254
<212> TYPE: PRT
<213> ORGANISM: Escherichia coli

<400> SEQUENCE: 86

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr Arg Lys His Glu Ile Asp Ala Ala Val Glu His Ile

```
                65                  70                  75                  80
Glu Thr Asp Phe Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 87
<211> LENGTH: 254
<212> TYPE: PRT
<213> ORGANISM: Escherichia coli

<400> SEQUENCE: 87

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
        50                  55                  60

Phe Asn Val Thr Arg Lys His Glu Ile Asp Ala Ala Val Glu His Ile
65                  70                  75                  80

Glu Thr Asp Ile Gly Thr Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg Arg Met Val Glu Arg Lys Ala Gly Lys Val Ile Asn Ile Gly
    130                 135                 140

Ser Met Gln Cys Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Ala Glu Asp Glu Ala Phe Thr Ala Trp
```

-continued

```
                195                 200                 205
Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 88
<211> LENGTH: 254
<212> TYPE: PRT
<213> ORGANISM: Escherichia coli

<400> SEQUENCE: 88

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Val Pro
50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Glu Phe Val Asn
225                 230                 235                 240

Gly His Leu Leu Phe Val Asp Gly Gly Met Leu Val Ala Leu
                245                 250

<210> SEQ ID NO 89
<211> LENGTH: 254
<212> TYPE: PRT
<213> ORGANISM: Escherichia coli

<400> SEQUENCE: 89

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
                20                  25                  30
```

```
Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Val Pro
 50                  55                  60

Phe Asn Val Thr His Lys His Glu Ile Asp Ala Ala Val Glu His Ile
 65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg Arg Met Val Glu Arg Lys Ala Gly Lys Val Ile Asn Ile Gly
        130                 135                 140

Ser Met Gln Cys Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 90
<211> LENGTH: 254
<212> TYPE: PRT
<213> ORGANISM: Escherichia coli

<400> SEQUENCE: 90

Met Asn Asp Leu Phe Ser Leu Ala Gly Lys Asn Ile Leu Ile Thr Gly
 1                   5                  10                  15

Ser Ala Gln Gly Ile Gly Phe Leu Leu Ala Thr Gly Leu Gly Lys Tyr
                20                  25                  30

Gly Ala Gln Ile Ile Ile Asn Asp Ile Thr Ala Glu Arg Ala Glu Leu
            35                  40                  45

Ala Val Glu Lys Leu His Gln Asp Gly Ile Gln Ala Val Ala Ala Pro
 50                  55                  60

Phe Asn Val Thr His Lys His Glu Ile Asp Ala Ala Val Glu His Ile
 65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
        130                 135                 140

Ser Met Gln Ser Glu Leu Gly Arg Asp Thr Thr Thr Pro Tyr Ala Ala
145                 150                 155                 160
```

```
Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 91
<211> LENGTH: 254
<212> TYPE: PRT
<213> ORGANISM: Escherichia coli

<400> SEQUENCE: 91

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Glu Ala Val Ala Val Pro
    50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 92
<211> LENGTH: 254
<212> TYPE: PRT
<213> ORGANISM: Escherichia coli
```

<400> SEQUENCE: 92

```
Met Asn Asp Leu Phe Ser Leu Ala Gly Lys Asn Ile Leu Ile Thr Gly
1               5                   10                  15
Ser Ala Gln Gly Ile Gly Phe Leu Leu Ala Thr Gly Leu Gly Lys Tyr
            20                  25                  30
Gly Ala Gln Ile Ile Ile Asn Asp Ile Thr Ala Glu Arg Ala Glu Leu
        35                  40                  45
Ala Val Glu Lys Leu His Gln Glu Gly Ile Gln Ala Val Ala Ala Pro
    50                  55                  60
Phe Asn Val Thr Arg Lys His Glu Ile Asp Ala Ala Val Glu His Ile
65                  70                  75                  80
Glu Thr Asp Ile Gly Thr Ile Asp Val Leu Val Asn Asn Ala Ala Ile
                85                  90                  95
Gln Arg Arg His Pro Phe Thr Glu Phe Pro Glu Gln Glu Trp Asn Asp
            100                 105                 110
Val Ile Ala Val Asn Gln Thr Ala Val Phe Leu Val Ser Gln Ala Val
        115                 120                 125
Thr Arg His Met Val Glu Arg Lys Ala Gly Lys Val Ile Asn Ile Cys
    130                 135                 140
Ser Met Gln Ser Glu Leu Gly Arg Asp Thr Thr Thr Pro Tyr Ala Ala
145                 150                 155                 160
Ser Lys Gly Ala Val Lys Met Leu Thr Arg Gly Met Cys Val Glu Leu
                165                 170                 175
Ala Arg His Asn Ile Gln Val Asn Gly Ile Ala Pro Gly Tyr Phe Lys
            180                 185                 190
Thr Glu Met Thr Lys Ala Leu Val Glu Asp Glu Ala Phe Thr Ala Trp
        195                 200                 205
Leu Cys Lys Arg Thr Pro Ala Ala Arg Trp Gly Asp Pro Gln Glu Leu
    210                 215                 220
Ile Gly Ala Ala Val Phe Leu Ser Ser Lys Ala Ser Asp Phe Val Asn
225                 230                 235                 240
Gly His Leu Leu Phe Val Asp Gly Gly Met Leu Val Ala Leu
                245                 250
```

<210> SEQ ID NO 93
<211> LENGTH: 254
<212> TYPE: PRT
<213> ORGANISM: Escherichia coli

<400> SEQUENCE: 93

```
Met Asn Asp Leu Phe Ser Leu Ala Gly Lys Asn Ile Leu Ile Thr Gly
1               5                   10                  15
Ser Ala Gln Gly Ile Gly Phe Leu Leu Ala Thr Gly Leu Gly Lys Tyr
            20                  25                  30
Gly Ala Gln Ile Ile Ile Asn Asp Ile Thr Ala Glu Arg Ala Glu Leu
        35                  40                  45
Ala Val Glu Lys Leu His Gln Glu Gly Ile Gln Ala Val Ala Ala Pro
    50                  55                  60
Phe Asn Val Thr Arg Lys His Glu Ile Asp Ala Ala Val Glu His Ile
65                  70                  75                  80
Glu Thr Asp Ile Gly Thr Ile Asp Val Leu Val Asn Asn Ala Ala Ile
                85                  90                  95
Gln Arg Leu His Pro Phe Thr Glu Phe Pro Glu Gln Glu Trp Asn Asp
            100                 105                 110
```

```
Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
        210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250
```

<210> SEQ ID NO 94
<211> LENGTH: 254
<212> TYPE: PRT
<213> ORGANISM: Escherichia coli

<400> SEQUENCE: 94

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Pro
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Ser Leu Val Ser Gln Ala Val
            115                 120                 125

Thr Arg Arg Met Val Glu Arg Lys Ala Gly Lys Val Ile Asn Ile Gly
130                 135                 140

Ser Met Gln Cys Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
        210                 215                 220

Ile Gly Ala Ala Val Phe Leu Ser Ser Lys Ala Ser Asp Phe Val Asn
225                 230                 235                 240
```

Gly His Leu Leu Phe Val Asp Gly Gly Met Leu Val Ala Leu
                245                 250

<210> SEQ ID NO 95
<211> LENGTH: 254
<212> TYPE: PRT
<213> ORGANISM: Escherichia coli

<400> SEQUENCE: 95

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Ala Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Asp His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Tyr Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 96
<211> LENGTH: 254
<212> TYPE: PRT
<213> ORGANISM: Escherichia coli

<400> SEQUENCE: 96

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Glu Ala Val Ala Ala Pro
    50                  55                  60

Phe Asn Val Thr His Lys His Glu Ile Asp Ala Ala Val Glu His Ile

```
                65                  70                  75                  80
Glu Thr Asp Ile Gly Thr Ile Asp Val Leu Val Asn Asn Ala Ala Ile
                    85                  90                  95
Gln Arg Arg His Pro Phe Thr Glu Phe Pro Glu Gln Glu Trp Asn Asp
                100                 105                 110
Val Ile Ala Val Asn Gln Thr Ala Val Phe Leu Val Ser Gln Ala Val
                115                 120                 125
Thr Arg His Met Val Glu Arg Lys Ala Gly Lys Val Ile Asn Ile Cys
                130                 135                 140
Ser Ile Gln Ser Glu Leu Gly Arg Asp Thr Thr Thr Pro Tyr Ala Ala
145                 150                 155                 160
Ser Lys Gly Ala Val Lys Met Leu Thr Arg Gly Met Cys Val Glu Leu
                165                 170                 175
Ala Arg His Asn Ile Gln Val Asn Gly Ile Ala Pro Gly Tyr Phe Lys
                180                 185                 190
Thr Glu Met Thr Lys Ala Leu Val Glu Asp Glu Ala Phe Thr Ala Trp
                195                 200                 205
Leu Cys Lys Arg Thr Pro Ala Ala Arg Trp Gly Asp Pro Gln Glu Leu
                210                 215                 220
Ile Gly Ala Ala Val Phe Leu Ser Ser Lys Ala Ser Asp Phe Val Asn
225                 230                 235                 240
Gly His Leu Leu Phe Val Asp Leu Gly Met Leu Val Ala Leu
                245                 250

<210> SEQ ID NO 97
<211> LENGTH: 254
<212> TYPE: PRT
<213> ORGANISM: Escherichia coli

<400> SEQUENCE: 97

Met Asn Asp Leu Phe Ser Leu Ala Gly Lys Asn Ile Leu Ile Thr Gly
1               5                   10                  15
Ser Ala Gln Gly Ile Gly Phe Leu Leu Ala Thr Gly Leu Gly Lys Tyr
                20                  25                  30
Gly Ala Gln Ile Ile Ile Asn Asp Ile Thr Ala Glu Arg Ala Glu Leu
            35                  40                  45
Ala Val Glu Lys Leu His Gln Glu Gly Ile Glu Ala Val Ala Ala Pro
        50                  55                  60
Phe Asn Val Thr His Lys His Glu Ile Asp Ala Ala Val Glu His Ile
65                  70                  75                  80
Glu Thr Asp Ile Gly Thr Ile Asp Val Leu Val Asn Asn Ala Ala Ile
                    85                  90                  95
Gln Arg Arg His Pro Phe Thr Glu Phe Pro Glu Gln Glu Trp Asn Asp
                100                 105                 110
Val Ile Ala Val Asn Gln Thr Ala Val Phe Leu Val Ser Gln Ala Val
                115                 120                 125
Thr Arg His Met Val Glu Arg Lys Thr Gly Lys Val Ile Asn Ile Cys
                130                 135                 140
Ser Ile Gln Ser Glu Leu Gly Arg Asp Thr Thr Thr Pro Tyr Ala Ala
145                 150                 155                 160
Ser Lys Gly Ala Val Lys Met Leu Thr Arg Gly Met Cys Val Glu Leu
                165                 170                 175
Ala Arg His Asn Ile Gln Val Asn Gly Ile Ala Pro Gly Tyr Phe Lys
                180                 185                 190
Thr Glu Met Thr Lys Ala Leu Val Glu Asp Glu Ala Phe Thr Ala Trp
```

```
                    195                 200                 205
Leu Cys Lys Arg Thr Pro Ala Ala Arg Trp Gly Asp Pro Gln Glu Leu
            210                 215                 220

Ile Gly Ala Ala Val Ser Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 98
<211> LENGTH: 254
<212> TYPE: PRT
<213> ORGANISM: Escherichia coli

<400> SEQUENCE: 98

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Ile Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 99
<211> LENGTH: 254
<212> TYPE: PRT
<213> ORGANISM: Escherichia coli

<400> SEQUENCE: 99

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30
```

Gly Ala Gln Ile Ile Ile Asn Asp Ile Thr Ala Glu Arg Ala Glu Leu
            35                  40                  45

Ala Val Glu Lys Leu His Gln Glu Gly Ile Gln Ala Val Ala Ala Pro
 50                  55                  60

Phe Asn Val Thr His Lys His Glu Ile Asp Ala Ala Val Glu His Ile
 65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
                100                 105                 110

Val Ile Ala Val Asn Gln Thr Ala Val Phe Leu Val Ser Gln Ala Val
                115                 120                 125

Thr Arg His Met Val Glu Arg Lys Ala Gly Lys Val Ile Asn Ile Cys
            130                 135                 140

Ser Met Gln Ser Glu Leu Gly Arg Asp Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
                180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Glu Phe Val Asn
225                 230                 235                 240

Gly His Leu Leu Phe Val Asp Gly Gly Met Leu Val Ala Leu
                245                 250

<210> SEQ ID NO 100
<211> LENGTH: 254
<212> TYPE: PRT
<213> ORGANISM: Escherichia coli

<400> SEQUENCE: 100

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
            35                  40                  45

Ala Val Asp Lys Leu His Gln Glu Gly Ile Gln Ala Val Ala Val Pro
 50                  55                  60

Phe Asn Val Thr His Lys His Glu Ile Asp Ala Ala Val Glu His Ile
 65                  70                  75                  80

Glu Lys Asn Ile Gly Pro Ile Asp Val Leu Val Asn Thr Ala Gly Ile
                85                  90                  95

Gln Arg Arg Phe Pro Phe Thr Glu Phe Pro Gln Gln Glu Trp Asn Glu
                100                 105                 110

Val Ile Ala Val Asn Gln Thr Ala Val Phe Leu Val Ser Gln Ala Val
                115                 120                 125

Thr Arg Arg Met Val Glu Arg Lys Ala Gly Lys Val Ile Asn Ile Gly
            130                 135                 140

Ser Met Gln Cys Glu Leu Gly Arg Asp Thr Ile Thr Pro Tyr Ala Ala
145                 150                 155                 160

```
Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Gly Val Phe Leu Ser Ser Lys Ala Ser Asp Phe Val Asn
225                 230                 235                 240

Gly His Leu Leu Phe Val Asp Gly Gly Met Leu Val Ala Leu
            245                 250

<210> SEQ ID NO 101
<211> LENGTH: 254
<212> TYPE: PRT
<213> ORGANISM: Escherichia coli

<400> SEQUENCE: 101

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr Arg Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Ile
        115                 120                 125

Thr Arg Arg Met Val Glu Arg Lys Ala Gly Lys Val Ile Asn Ile Gly
    130                 135                 140

Ser Met Gln Cys Glu Leu Gly Arg Asp Thr Ile Thr Pro Tyr Ala Ala
145                 150                 155                 160

Ser Lys Gly Ala Val Lys Met Leu Thr Arg Gly Met Cys Val Glu Leu
            165                 170                 175

Ala Arg His Asn Ile Gln Val Asn Gly Ile Ala Pro Gly Tyr Phe Ile
            180                 185                 190

Thr Glu Met Thr Lys Ala Leu Val Glu Asp Glu Ala Phe Thr Ala Trp
            195                 200                 205

Leu Cys Lys Arg Thr Pro Ala Ala Arg Trp Gly Asp Pro Gln Glu Leu
            210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
            245                 250

<210> SEQ ID NO 102
<211> LENGTH: 254
<212> TYPE: PRT
<213> ORGANISM: Escherichia coli
```

<400> SEQUENCE: 102

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
50                  55                  60

Phe Asn Val Thr His Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Ala Glu Asp Glu Ala Phe Thr Ala Trp
        195                 200                 205

Leu Cys Lys Arg Thr Pro Ala Ala Arg Trp Gly Asp Pro Gln Glu Leu
210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250

<210> SEQ ID NO 103
<211> LENGTH: 254
<212> TYPE: PRT
<213> ORGANISM: Escherichia coli

<400> SEQUENCE: 103

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Glu Ala Val Ala Ala Pro
50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Gly Ile
                85                  90                  95

Gln Arg Arg His Pro Phe Thr Glu Phe Pro Glu Gln Glu Trp Asn Asp
            100                 105                 110

```
Val Ile Ala Val Asn Gln Thr Ala Val Phe Leu Val Ser Gln Ala Val
            115                 120                 125

Thr Arg His Met Val Glu Arg Lys Ala Gly Lys Val Ile Asn Ile Gly
    130                 135                 140

Ser Met Gln Cys Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Leu Gly Met Leu Val Ala Leu
                245                 250

<210> SEQ ID NO 104
<211> LENGTH: 254
<212> TYPE: PRT
<213> ORGANISM: Escherichia coli

<400> SEQUENCE: 104

Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
65                  70                  75                  80

Glu Lys Asp Ile Gly Pro Ile Asp Val Leu Val Asn Asn Ala Ser Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Met Gln Ser Glu Leu Gly Arg Asp Thr Thr Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240
```

```
Gly His Leu Leu Phe Val Asp Gly Gly Met Leu Val Ala Leu
            245                 250
```

<210> SEQ ID NO 105
<211> LENGTH: 254
<212> TYPE: PRT
<213> ORGANISM: Escherichia coli

<400> SEQUENCE: 105

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr Arg Lys His Glu Ile Asp Ala Ala Val Glu His Ile
65                  70                  75                  80

Glu Thr Asp Ile Gly Thr Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Ile Gln Ser Glu Leu Gly Arg Asp Thr Leu Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Val
                245                 250
```

<210> SEQ ID NO 106
<211> LENGTH: 254
<212> TYPE: PRT
<213> ORGANISM: Escherichia coli

<400> SEQUENCE: 106

```
Met Asn Asp Leu Phe Ser Leu Ala Gly Lys Asn Ile Leu Ile Thr Gly
1               5                   10                  15

Ser Ala Gln Gly Ile Gly Phe Leu Leu Ala Thr Gly Leu Gly Lys Tyr
            20                  25                  30

Gly Ala Gln Ile Ile Ile Asn Asp Ile Thr Ala Glu Arg Ala Glu Leu
        35                  40                  45

Ala Val Glu Lys Leu His Gln Glu Gly Ile Gln Ala Val Ala Ala Pro
    50                  55                  60

Phe Asn Val Thr His Lys His Glu Ile Asp Ala Ala Val Glu His Ile
```

-continued

```
65                  70                  75                  80
Glu Lys Asp Ile Gly Pro Ile Asp Val Leu Val Asn Asn Ala Ala Ile
                85                  90                  95

Gln Arg Arg His Pro Phe Thr Glu Phe Pro Glu Gln Glu Trp Asn Asp
            100                 105                 110

Val Ile Ala Val Asn Gln Thr Ala Val Phe Leu Val Ser Gln Ala Val
        115                 120                 125

Thr Arg His Met Val Glu Arg Lys Ala Gly Lys Val Ile Asn Ile Cys
    130                 135                 140

Ser Ile Gln Ser Glu Leu Gly Arg Asp Thr Leu Thr Pro Tyr Ala Ala
145                 150                 155                 160

Ser Lys Gly Ala Val Lys Met Leu Thr Arg Gly Met Cys Val Glu Leu
                165                 170                 175

Ala Arg His Asn Ile Gln Val Asn Gly Ile Ala Pro Gly Tyr Phe Lys
            180                 185                 190

Thr Glu Met Thr Lys Ala Leu Val Glu Asp Glu Ala Phe Thr Ala Trp
        195                 200                 205

Leu Cys Lys Arg Thr Pro Ala Ala Arg Trp Gly Asp Pro Gln Glu Leu
    210                 215                 220

Ile Gly Ala Ala Val Phe Leu Ser Ser Lys Ala Ser Asp Phe Val Asn
225                 230                 235                 240

Gly His Leu Leu Phe Val Asp Gly Gly Met Leu Val Ala Leu
                245                 250
```